US010563070B2

(12) United States Patent
Mitsuhashi et al.

(10) Patent No.: US 10,563,070 B2
(45) Date of Patent: Feb. 18, 2020

(54) SILANE COMPOUND CONTAINING PERFLUORO(POLY)ETHER GROUP

(71) Applicant: DAIKIN INDUSTRIES, LTD., Osaka-shi, Osaka (JP)

(72) Inventors: Hisashi Mitsuhashi, Settsu (JP); Takashi Nomura, Settsu (JP); Akinari Sugiyama, Settsu (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 511 days.

(21) Appl. No.: 14/440,192

(22) PCT Filed: Oct. 31, 2013

(86) PCT No.: PCT/JP2013/079608
§ 371 (c)(1),
(2) Date: May 1, 2015

(87) PCT Pub. No.: WO2014/069592
PCT Pub. Date: May 8, 2014

(65) Prior Publication Data
US 2015/0307719 A1    Oct. 29, 2015

(30) Foreign Application Priority Data

Nov. 5, 2012  (JP) ................................ 2012-243360
Feb. 8, 2013  (JP) ................................ 2013-023133
Apr. 12, 2013 (JP) ................................ 2013-083921

(51) Int. Cl.
C09D 5/16    (2006.01)
C07F 7/08    (2006.01)
C07F 7/18    (2006.01)

(52) U.S. Cl.
CPC ............ C09D 5/1625 (2013.01); C07F 7/081 (2013.01); C07F 7/0827 (2013.01); C07F 7/1804 (2013.01); C07F 7/188 (2013.01)

(58) Field of Classification Search
CPC .... C07F 7/0818; C07F 7/0827; C07F 7/1868; C07F 7/188; C08G 65/007; C08G 65/336; C09D 171/02; C09D 5/16; C09D 5/1625
See application file for complete search history.

(56) References Cited

U.S. PATENT DOCUMENTS

2002/0137842 A1    9/2002  Sato et al.
2007/0149746 A1*   6/2007  Yamane .................... C07F 7/21
                                                528/42
2010/0076211 A1    3/2010  Yamane et al.
2011/0098402 A1*   4/2011  Yamane ............... C08G 65/007
                                                524/521
2012/0077041 A1    3/2012  Yamane et al.

FOREIGN PATENT DOCUMENTS

| EP | 1 036 809 A1 | 9/2000 |
| EP | 1 059 320 A2 | 12/2000 |
| EP | 1801144 A2 | 6/2007 |
| EP | 1897899 A1 | 3/2008 |
| EP | 1995289 A1 | 11/2008 |
| EP | 2725078 A1 | 4/2014 |
| JP | 2000-226413 A | 8/2000 |
| JP | 2000-327772 A | 11/2000 |
| JP | 2001-354764 A | 12/2001 |
| JP | 2002-194201 A | 7/2002 |
| JP | 2002-293919 A | 10/2002 |
| JP | 2002-348370 A | 12/2002 |
| JP | 2003-64348 A | 3/2003 |
| JP | 2008-537557 A | 9/2008 |
| JP | 2010-47516 A | 3/2010 |
| JP | 2012-72272 A | 4/2012 |
| JP | 2012-197395 A | 10/2012 |
| JP | 2013-227279 A | 11/2013 |
| KR | 2000-0062943 A | 10/2000 |
| WO | 2006/107082 A1 | 10/2006 |
| WO | 2013/146112 A1 | 10/2013 |

OTHER PUBLICATIONS

Yuuki Fujii et al., "Titanocene-catalyzed alkylalive dimerization of vinyl Grignard reagent using alkyl halides", Chemical Communications, 2008, pp. 5836-5838, vol. 44.
International Search Report for PCT/JP2013/079609 dated Feb. 4, 2014.
International Preliminary Report on Patentability dated May 5, 2015, issued by the International Searching Authority in counterpart International Application No. PCT/JP2013/079608.
Communication dated Jun. 6, 2016, from the European Patent Office in counterpart European Application No. 13852235.4.

* cited by examiner

*Primary Examiner* — Michael B Nelson
(74) *Attorney, Agent, or Firm* — Sughrue Mion, PLLC

(57) ABSTRACT

A perfluoro(poly)ether group containing silane compound represented by the formula (1a) or the formula (1b):

$$A-Rf-X-SiQ_kY_{3-k} \quad (1a)$$

$$Y_{3-k}Q_kSi-X-Rf-X-SiQ_kY_{3-k} \quad (1b)$$

as defined herein. Also disclosed is a process for producing the compound, a surface-treating agent containing the compound, a pellet containing the surface-treating agent and an optical member including a base material and a layer formed on a surface of the base material from the compound.

32 Claims, No Drawings

SILANE COMPOUND CONTAINING PERFLUORO(POLY)ETHER GROUP

CROSS REFERENCE TO RELATED APPLICATIONS

This application is a National Stage of International Application No. PCT/JP2013/079608 filed Oct. 31, 2013, claiming priority based on Japanese Patent Application Nos. 2012-243360 filed Nov. 5, 2012, 2013-023133 filed Feb. 8, 2013, and 2013-083921 filed Apr. 12, 2013, the contents of all of which are incorporated herein by reference in their entirety.

TECHNICAL FIELD

The present invention relates to a perfluoro(poly)ether group containing silane compound. The present invention also relates to a method of producing the perfluoro(poly)ether group containing silane compound and a surface-treating agent comprising it.

BACKGROUND ART

A certain fluorine-containing silane compound is known to be able to provide excellent water-repellency, oil-repellency, antifouling property, or the like when it is used on a surface treatment of a base material. A layer (hereinafter, referred to as a "surface-treating layer") formed from the surface-treating agent comprising a fluorine-containing silane compound is applied to various base materials such as a glass, a plastic, a fiber and a building material as a so-called functional thin film.

As such fluorine-containing silane compound, a perfluoropolyether group containing silane compound which has a perfluoropolyether group in its molecular main chain and a hydrolyzable group bonding to a Si atom in its molecular terminal or terminal portion is known. For example, Patent Literature 1 describes a fluoro-containing silane compound wherein a main backbone having a perfluoropolyether group and a Si atom having a hydrolyzable group are connected via a linker moiety containing a siloxane bond. Patent Literature 2 describes a fluoro-containing silane compound wherein the compound has an amide at the end of a main backbone having a perfluoropolyether group, and 2 Si atoms having a hydrolyzable group are bonded to an N atom of the amide via a linker. Furthermore, Patent Literature 3 describes a fluoro-containing silane compound which having a plurality of Si atoms having a hydrolyzable group at the end of a main backbone having a perfluoropolyether group.

PRIOR ART LITERATURE

Patent Literature

Patent Literature 1: JP 2002-348370 A
Patent Literature 2: JP 2000-327772 A
Patent Literature 3: JP 2012-72272 A

SUMMARY OF THE INVENTION

Problem to be Solved by the Invention

The surface-treating layer is requested for high durability to provide a base material with a desired function for a long time. The layer formed from the surface-treating agent containing the perfluoropolyether group containing silane compound has been suitably used in an optical member such as glasses, touch panel or the like which is required to have light permeability or transparency since it can exert the above functions even in form of a thin film. In particular, in these uses, the friction durability is required to be further improved.

However, a layer formed from a surface-treating agent containing a conventional perfluoropolyether group containing silane compound described above is no longer necessarily enough to meet the increasing demand to improve the friction durability.

An object of the present invention is to provide a novel perfluoro(poly)ether group containing silane compound which is able to form a layer having water-repellency, oil-repellency and antifouling property as well as high friction durability. An object of the present invention is also to provide a process for producing the perfluoro(poly)ether group containing silane compound, a surface-treating agent containing it, and the like. Furthermore, an object of the present invention is to provide an intermediate compound for producing the perfluoro(poly)ether group containing silane compound and a process for producing the intermediate compound.

Means to Solve the Problem

As a result of intensively studying, the inventors of the present invention have found that a perfluoro(poly)ether group containing silane compound is able to form a surface-treating layer having excellent friction durability in addition to water-repellency, oil-repellency, antifouling property, wherein the compound has a Si atom at the end of a main backbone having a perfluoro(poly)ether group, and at least one other Si atom is connected to the Si atom via a linker, and a hydroxyl group or a hydrolyzable group is bonded to some of the other Si atom, and the inventors reach the present invention.

Therefore, according to first aspect of the present invention, there is provided a perfluoro(poly)ether group containing silane compound of the formula (1a) or the formula (1b):

$$A\text{-Rf}\text{—}X\text{—}SiQ_kY_{3-k} \quad (1a)$$

$$Y_{3-k}Q_kSi\text{—}X\text{—}Rf\text{—}X\text{—}SiQ_kY_{3-k} \quad (1b)$$

wherein A represents a $C_{1-16}$ alkyl which may be substituted by one or more fluorine atoms;

Rf represents —$(OC_4F_8)_a$—$(OC_3F_6)_b$—$(OC_2F_4)_c$—$(OCF_2)_d$—

wherein a, b, c and d are each independently an integer of 0 or more and 200 or less, the sum of a, b, c and d is 1 or more and the occurrence order of the respective repeating units in parentheses with the subscript a, b, c or d is not limited in the formula;

X represents a divalent organic group;

Y represents, each independently at each occurrence, a hydroxyl group, a hydrolyzable group, or a hydrocarbon group;

Q represents, each independently at each occurrence, —Z—$SiR^1_nR^2_{3-n}$;

Z represents, each independently at each occurrence, a divalent organic group: with the proviso that Z is not a group which forms a siloxane bond together with a Si atom present in the end of a molecular backbone of the formula (1a) or the formula (1b), $R^1$ represents, each independently at each occurrence, a hydroxyl group or a hydrolyzable group;

$R^2$ represents, each independently at each occurrence, a $C_{1-22}$ alkyl group or Q';

Q' has the same definition as that of Q;

n is, each independently in each Q and Q', an integer selected from 0-3, and the total sum of n one or more;

in Q, the number of Si atoms which are straightly linked via the Z group is up to five;

k is an integer each independently selected from 1-3.

According to second aspect of the present invention, there is provided a process for producing the perfluoro(poly)ether group containing silane compound of the formula (1a) or the formula (1b) described above, which comprises the following steps:

Step (1): reacting a compound of the formula (1a-1) or the formula (1b-1):

$$A\text{-Rf}\text{—}X'\text{—}CH\text{=}CH_2 \quad (1a\text{-}1)$$

$$CH_2\text{=}CH\text{—}X'\text{—}Rf\text{—}X'\text{—}CH\text{=}CH_2 \quad (1b\text{-}1)$$

wherein A and Rf are as defined above, and X' represents a divalent organic group;

with $HSiM_3$ wherein M is each independently a halogen atom or a $C_{1-6}$ alkoxy group, to obtain a compound of the formula (1a-2) or the formula (1b-2):

$$A\text{-Rf}\text{—}X'\text{—}CH_2\text{—}CH_2\text{—}SiM_3 \quad (1a\text{-}2)$$

$$M_3Si\text{—}CH_2CH_2\text{—}X'\text{—}Rf\text{—}X'\text{—}CH_2\text{—}SiM_3 \quad (1b\text{-}2)$$

wherein A, Rf, X' and M are as defined above;

Step (2): reacting a compound of the formula (1a-2) or the formula (1b-2) with a compound of Formula: $Hal\text{-}J\text{-}Z'\text{—}CH\text{=}CH_2$ wherein Z' represents a bond or a divalent organic group, J represents Mg, Cu, Pd or Zn, and Hal represents a halogen atom, and optionally a compound of Formula: $Y_hL$ wherein Y is as defined above, L represents a group which is able to bind to Y, and h is an integer of 1-3, to obtain a compound of the formula (1a-3) or the formula (1b-3):

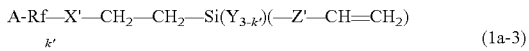

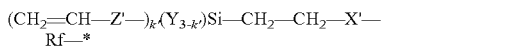

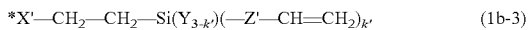

wherein A, Rf, X', Y and Z' are as defined above, and k' is an integer of 1-3; and Step (3): reacting a compound of the formula (1a-3) or the formula (1b-3) with $HSiM_3$ wherein M is as defined above, and/or a compound of Formula: $R^1_iL'$ wherein $R^1$ is as defined in claim 1, L' represents a group which is able to bind to R', and i is an integer of 1-3, and optionally a compound of Formula: $R^{2'}_jL''$ wherein $R^{2'}$ represents a $C_{1-22}$ alkyl group, L" represents a group which is able to bind to $R^{2'}$, and j is an integer of 1-3.

According to third aspect of the present invention, there is provided a compound of the formula (1a-3') or the formula (1b-3'):

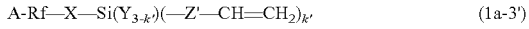

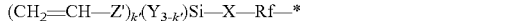

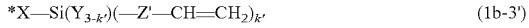

wherein A represents a $C_{1-16}$ alkyl which may be substituted by one or more fluorine atoms;

Rf represents $\text{—}(OC_4F_8)_a\text{—}(OC_3F_6)_b\text{—}(OC_2F_4)_c\text{—}(OCF_2)_d\text{—}$ wherein a, b, c and d are each independently an integer of 0 or more and 200 or less, the sum of a, b, c and d is 1 or more, and the occurrence order of the respective repeating units in parentheses with the subscript a, b, c or d is not limited in the formula;

X represents a divalent organic group;

Y represents, each independently at each occurrence, a hydroxyl group, a hydrolyzable group, or a hydrocarbon group; and Z' is a bond or a divalent organic group.

The compound is an intermediate compound in the process for producing the perfluoro(poly)ether group containing silane compound of the formula (1a) or the formula (1b).

According to fourth aspect of the present invention, there is provided a process for producing the compound of the formula (1a-3') or the formula (1b-3') described above which comprises a step of:

reacting a compound of the formula (1a-2') or the formula (1b-2'):

$$A\text{-Rf}\text{—}X\text{—}SiM_3 \quad (1a\text{-}2')$$

$$M_3Si\text{—}X\text{—}Rf\text{—}X\text{—}SiM_3 \quad (1b\text{-}2')$$

wherein A, Rf, X and M are as defined above, with a compound of

Formula: $Hal\text{-}J\text{-}Z'\text{—}CH\text{=}CH_2$ wherein Z' is as defined above, J represents Mg, Cu, Pd or Zn, and Hal represents a halogen atom, and optionally a compound of Formula: $Y_hL$ wherein Y is as defined above, L represents a group which is able to bind to Y, and h is an integer of 1-3.

According to fifth aspect of the present invention, there is provided a surface-treating agent comprising at least one the perfluoro(poly)ether group containing silane compound of the formula (1a) and/or the formula (1b) described above.

According to sixth aspect of the present invention, there is provided an article comprising a base material and a layer which is formed on a surface of the base material from the perfluoro(poly)ether group containing silane compound of the formula (1a) and/or the formula (1b) described above or the surface-treating agent described above.

Effect of the Invention

According to the present invention, there is provided a novel perfluoropolyether group containing silane compound. Furthermore, there is provided a surface-treating agent obtained by using the perfluoropolyether group containing silane compound. By using them, the surface-treating layer having water-repellency, oil-repellency and antifouling property as well as excellent friction durability can be formed.

EMBODIMENTS TO CARRY OUT THE INVENTION

Hereinafter, the compound of the present invention will be described.

The term "a divalent organic group" as used herein represents a divalent organic group containing a carbon atom. Examples of the divalent organic group include, but are not particularly limited to, a divalent group obtained by removing further one hydrogen atom from a hydrocarbon group.

The term "a hydrocarbon group" as used herein represents a group containing a carbon atom and a hydrogen atom.

Examples of the hydrocarbon group include, but are not particularly limited to, a hydrocarbon group having 1-carbon atoms which may be substituted by one or more substituents, for example, an aliphatic hydrocarbon group, an aromatic hydrocarbon group, and the like. The "aliphatic hydrocarbon group" may be straight, branched or cyclic, and may be saturated or unsaturated. The hydrocarbon group may contain one or more ring structures. It is noted that the hydrocarbon group may have one or more N, O, S, Si, amide, sulfonyl, siloxane, carbonyl, carbonyloxy, or the like at its end or in its molecular chain.

As used herein, examples of the substituent of the "hydrocarbon group" include, but are not particularly limited to, for example a halogen atom; and a $C_{1-6}$ alkyl group, a $C_{2-6}$ alkenyl group, a $C_{2-6}$ alkynyl group, a $C_{3-10}$ cycloalkyl group, a $C_{3-10}$ unsaturated cycloalkyl group, a 5-10 membered heterocyclyl group, a 5-10 membered unsaturated heterocyclyl group, a $C_{6-10}$ aryl group, a 5-10 membered heteroaryl group, and the like which may be substituted by one or more halogen atoms.

The present invention provides a perfluoro(poly)ether group (hereinafter, also referred to as "PFPE") containing silane compound of the formula (1a) or the formula (1b) (hereinafter, also referred to as "a PFPE containing silane compound of the present invention".

(1a)

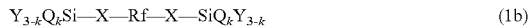
(1b)

In the above-mentioned formula (1a) and the formula (1b), A represents a $C_{1-16}$ alkyl which may be substituted by one or more fluorine atoms.

The "$C_{1-16}$ alkyl group" in the $C_{1-16}$ alkyl which may be substituted by one or more fluorine atoms is a straight or branched alkyl group having 1-16 carbon atoms, preferably a straight or branched alkyl group having 1-6 carbon atoms, in particular 1-3 carbon atoms, more preferably a straight alkyl group having 1-3 carbon atoms.

The above-mentioned A is preferably a $C_{1-16}$ alkyl substituted by one or more fluorine atoms, more preferably a $CF_2H$—$C_{1-15}$ perfluoroalkylene group, more preferably a $C_{1-16}$ perfluoroalkyl group.

The $C_{1-16}$ perfluoroalkyl group is a straight or branched perfluoroalkyl group having 1-16 carbon atoms, preferably a straight or branched perfluoroalkyl group having 1-6 carbon atoms, in particular 1-3 carbon atoms, more preferably a straight perfluoroalkyl group having 1-3 carbon atoms, specifically —$CF_3$, —$CF_2CF_3$, or —$CF_2CF_2CF_3$.

In the above-mentioned formula (1a) and the formula (1b), Rf represents —$(OC_4F_8)_a$—$(OC_3F_6)_b$—$(OC_2F_4)_c$—$(OCF_2)_d$—, and corresponds to a perfluoro(poly)ether group. Herein, a, b, c and d are each independently 0 or an integer of 1 or more and are not particularly limited as long as the sum of a, b, c and d is 1 or more. Preferably, a, b, c and d are each independently an integer of 0 or more and 200 or less, for example an integer of 1 or more and 200 or less, more preferably each independently an integer of 0 or more and 100 or less, for example, an integer of 1 or more and 100 or less. More preferably, the sum of a, b, c and d is 10 or more, preferably 20 or more and 200 or less, preferably 100 or less. The occurrence order of the respective repeating units in parentheses with the subscript a, b, c or d is not limited in the formula. Among these repeating units, the —$(OC_4F_8)$— group may be any of —$(OCF_2CF_2CF_2CF_2)$—, —$(OCF(CF_3)CF_2CF_2)$—, —$(OCF_2CF(CF_3)CF_2)$—, —$(OCF_2CF_2CF(CF_3))$—, —$(OC(CF_3)_2CF_2)$—, —$(OCF_2C(CF_3)_2)$—, —$(OCF(CF_3)CF(CF_3))$—, —$(OCF(C_2F_5)CF_2)$— and —$(OCF_2CF(C_2F_5))$—, preferably —$(OCF_2CF_2CF_2CF_2)$—. The —$(OC_3F_6)$— group may be any of —$(OCF_2CF_2CF_2)$—, —$(OCF(CF_3)CF_2)$— and —$(OCF_2CF(CF_3))$—, preferably —$(OCF_2CF_2CF_2)$—. The —$(OC_2F_4)$— group may be any of —$(OCF_2CF_2)$— and —$(OCF(CF_3))$—, preferably —$(OCF_2CF_2)$—.

In one embodiment, Rf is —$(OC_3F_6)_b$— wherein b is an integer of 1 or more and 200 or less, preferably 10 or more and 100 or less, preferably —$(OCF_2CF_2CF_2)_b$— wherein b is as defined above.

In another embodiment, Rf is —$(OC_4F_8)_a$—$(OC_3F_6)_b$—$(OC_2F_4)_c$—$(OCF_2)_d$— wherein a and b are each independently an integer of 0 or more, or 1 or more and 30 or less, preferably 0 or more and 10 or less, and c and d are each independently an integer of 1 or more and 200 or less, preferably 10 or more and 100 or less. The sum of a, b, c and d is 10 or more, preferably 20 or more and 200 or less, preferably 100 or less. The occurrence order of the respective repeating units in parentheses with the subscript a, b, c or d is not limited in the formula. Preferably, Rf is —$(OCF_2CF_2CF_2CF_2)_a$—$(OCF_2CF_2CF_2)_b$—$(OCF_2CF_2)_c$—$(OCF_2)_d$— wherein a, b, c and d are as defined above.

In the above-mentioned formula (1a) and the formula (1b), X represents a divalent organic group. The X group is recognized to be a linker which connects a perfluoropolyether moiety (an A-Rf— moiety or a —Rf-moiety) providing mainly water-repellency and surface slip property and a silane moiety (a —$SiQ_kY_{3-k}$ moiety) providing an ability to bind to a base material by hydrolyzing in the compound of the formula (1a) and the formula (1b). Therefore, the X group may be any divalent organic group as long as the compound of the formula (1a) and the formula (1b) can be stably exist.

Examples of X include, but are not particularly limited to, for example a group of the following formula:

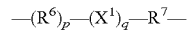

wherein:
$R^6$ represents —$(CH_2)_s$— or an o-, m- or p-phenylene group, preferably —$(CH_2)_s$—;
$R^7$ represents —$(CH_2)_t$— or an o-, m- or p-phenylene group, preferably —$(CH_2)_t$—;
$X^1$ represents —$(X^2)_r$—;
$X^2$ represents, each independently at each occurrence, a group selected from a group consisting of —O—, —S—, an o-, m- or p-phenylene group, —C(O)O—, —CONR$^5$—, —O—CONR$^5$—, —NR$^5$—, —Si(R$^3$)$_2$—, —(Si(R$^3$)$_2$O)$_m$—Si(R$^3$)$_2$— and —(CH$_2$)$_v$—;
$R^3$ represents, each independently at each occurrence, a phenyl group or a $C_{1-6}$ alkyl group, preferably a $C_{1-6}$ alkyl group, more preferably a methyl group;
$R^5$ represents, each independently at each occurrence, a hydrogen atom, a phenyl group or a $C_{1-6}$ alkyl group (preferably, a methyl group);
m is, each independently at each occurrence, an integer of 1-100, preferably an integer of 1-20;
v is, each independently at each occurrence, an integer of 1-20, preferably an integer of 1-6, more preferably an integer of 1-3;
s is an integer of 1-20, preferably an integer of 1-6, more preferably an integer of 1-3, further preferably 1 or 2;
t is an integer of 1-20, preferably an integer of 2-6, more preferably an integer of 2-3;
r is an integer of 1-10, preferably an integer of 1-5, more preferably an integer of 1-3;
p is 0 or 1; and
q is 0 or 1.

Preferably, the above-mentioned X may be
a $C_{1-20}$ alkylene group,
—$R^6$—$X^3$—$R^7$—, or
—$X^4$—$R^7$—
wherein $R^6$ and $R^7$ are as defined above.

More preferably, the above-mentioned X is
a $C_{1-20}$ alkylene group,
—$(CH_2)_s$—$X^3$—$(CH_2)_t$—, or
—$X^4$—$(CH_2)_t$—
wherein s and t are defined above.

In the above-mentioned formula, $X^3$ represents
—O—,
—S—,
—C(O)O—,
—$CONR^5$—,
—O—$CONR^5$—,
—$Si(R^3)_2$—,
—$(Si(R^3)_2O)_m$—$Si(R^3)_2$—,
—O—$(CH_2)_u$—$(Si(R^3)_2O)_m$—$Si(R^3)_2$—,
—$CONR^5$—$(CH_2)_u$—$(Si(R^3)_2O)_m$—$Si(R^3)_2$—,
—$CONR^5$—$(CH_2)_v$—$N(R^5)$—, or
—$CONR^5$-(o-, m- or p-phenylene)-$Si(R^3)_2$—
wherein $R^3$, $R^5$, m and v are as defined above,
u is an integer of 1-20, preferably an integer of 2-6, more preferably an integer 2-3. $X^3$ is preferably —O—.

In the above-mentioned formula, $X^4$ represents
—S—,
—C(O)O—,
—$CONR^5$—,
—$CONR^5$—$(CH_2)_u$—$(Si(R^3)_2O)_m$—$Si(R^3)_2$—,
—$CONR^5$—$(CH_2)_v$—$N(R^5)$—, or
—$CONR^5$-(o-, m- or p-phenylene)-$Si(R^3)_2$—.

More preferably, the above-mentioned X may be
a $C_{1-20}$ alkylene group,
—$(CH_2)_s$—$X^3$—$(CH_2)_t$—, or
—$X^4$—$(CH_2)_t$—,
wherein each symbol is as defined above.

Further preferably, the above-mentioned X is
a $C_{1-20}$ alkylene group,
—$(CH_2)_s$—O—$(CH_2)_t$—,
—$(CH_2)_s$—$(Si(R^3)_2O)_m$—$Si(R^3)_2$—$(CH_2)_t$—, or
—$(CH_2)_s$—O—$(CH_2)_u$—, —$(Si(R^3)_2O)_m$—$Si(R^3)_2$—$(CH_2)_t$—,
wherein each symbol is as defined above.

The above-mentioned X grope may be substituted by one or more substituents selected from a fluorine atom, a $C_{1-3}$ alkyl group and a $C_{1-3}$ fluoroalkyl group (preferably, a $C_{1-3}$ perfluoroalkyl group).

Specific examples of X include, for example:
—$CH_2O(CH_2)_2$—,
—$CH_2O(CH_2)_3$—,
—$CH_2O(CH_2)_6$—,
—$CH_2O(CH_2)_3Si(CH_3)_2OSi(CH_3)_2(CH_2)_2$—,
—$CH_2O(CH_2)_3Si(CH_3)_2O(Si(CH_3)_2O(Si(CH_3)_2(CH_2)_2$—,
—$CH_2O(CH_2)_3Si(CH_3)_2O(Si(CH_3)_2O)_2Si(CH_3)_2(CH_2)_2$—,
—$CH_2O(CH_2)_3Si(CH_3)_2O(Si(CH_3)_2O)_3Si(CH_3)_2(CH_2)_2$—,
—$CH_2O(CH_2)_3Si(CH_3)_2O(Si(CH_3)_2O)_{10}Si(CH_3)_2(CH_2)_2$—,
—$CH_2O(CH_2)_3Si(CH_3)_2O(Si(CH_3)_2O)_{20}Si(CH_3)_2(CH_2)_2$—,
—$(CH_2)_2$—
—$(CH_2)_3$—,
—$(CH_2)_4$—,
—$(CH_2)_6$—,
—$CONH$—$(CH_2)_3$—,
—$CON(CH_3)$—$(CH_2)_3$—,
—$CON(Ph)$-$(CH_2)_3$— wherein Ph represents a phenyl group,
—$CONH$—$(CH_2)_6$—,
—$CON(CH_3)$—$(CH_2)_6$—,
—$CON(Ph)$-$(CH_2)_6$— wherein Ph represents a phenyl group,
—$CONH$—$(CH_2)_2NH(CH_2)_3$—,
—$CONH$—$(CH_2)_6NH(CH_2)_3$—,
—$CH_2O$—$CONH$—$(CH_2)_3$—,
—$CH_2O$—$CONH$—$(CH_2)_6$—,
—S—$(CH_2)_3$—
—$(CH_2)_2S(CH_2)_3$—,
—$CONH$—$(CH_2)_3Si(CH_3)_2OSi(CH_3)_2(CH_2)_2$—,
—$CONH$—$(CH_2)_3Si(CH_3)_2OSi(CH_3)_2OSi(CH_3)_2(CH_2)_2$—,
—$CONH$—$(CH_2)_3Si(CH_3)_2O(Si(CH_3)_2O)_3Si(CH_3)_2(CH_2)_2$—,
—$CONH$—$(CH_2)_3Si(CH_3)_2O(Si(CH_3)_2O)_{10}Si(CH_3)_2(CH_2)_2$—,
—$CONH$—$(CH_2)_3Si(CH_3)_2O(Si(CH_3)_2O)_{20}Si(CH_3)_2(CH_2)_2$—,
—$C(O)O$—$(CH_2)_3$—,
—$C(O)O$—$(CH_2)_6$—,

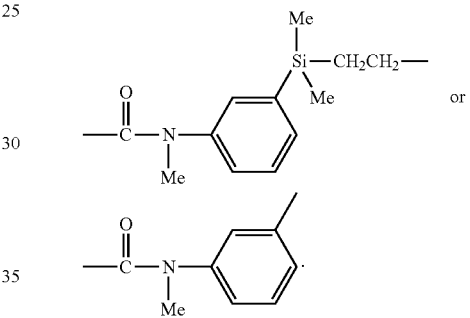

Other examples of the X include, for example the following groups:

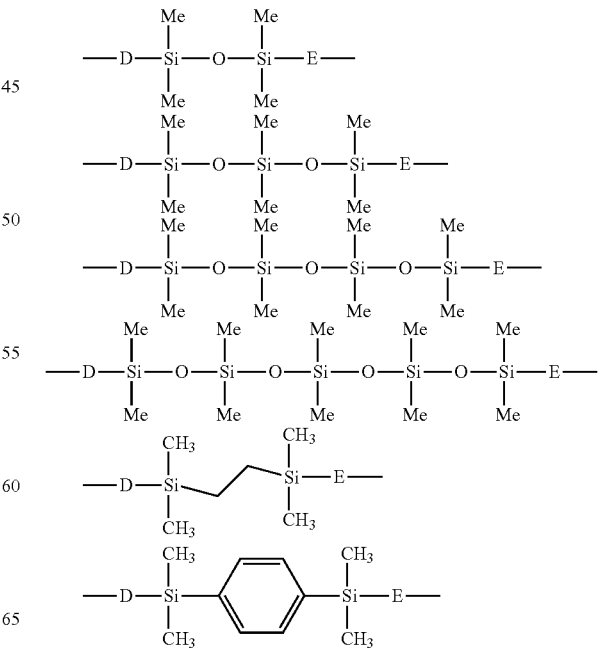

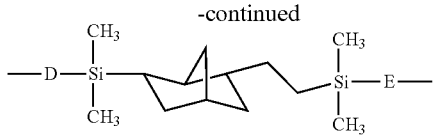

wherein D is a group selected from
—CH$_2$O(CH$_2$)$_2$—,
—CH$_2$O(CH$_2$)$_3$—,
—CF$_2$O(CH$_2$)$_3$—,
—(CH$_2$)$_2$—,
—(CH$_2$)$_3$—,
—(CH$_2$)$_4$—,
—CONH—(CH$_2$)$_3$—,
—CON(CH$_3$)—(CH$_2$)$_3$—,
—CON(Ph)-(CH$_2$)$_3$— wherein Ph represents a phenyl group, and

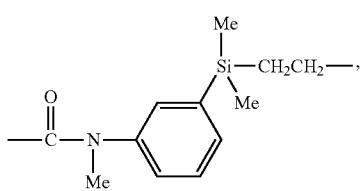

E is —(CH$_2$)$_n$— wherein n is an integer of 2-6, and
D binds to A-Rf— of the main backbone of the formula (1a) and the formula (1b), and E binds to a Si atom in the main backbone of the formula (1a) and the formula (1b).

Further other examples of the X group include the following groups:

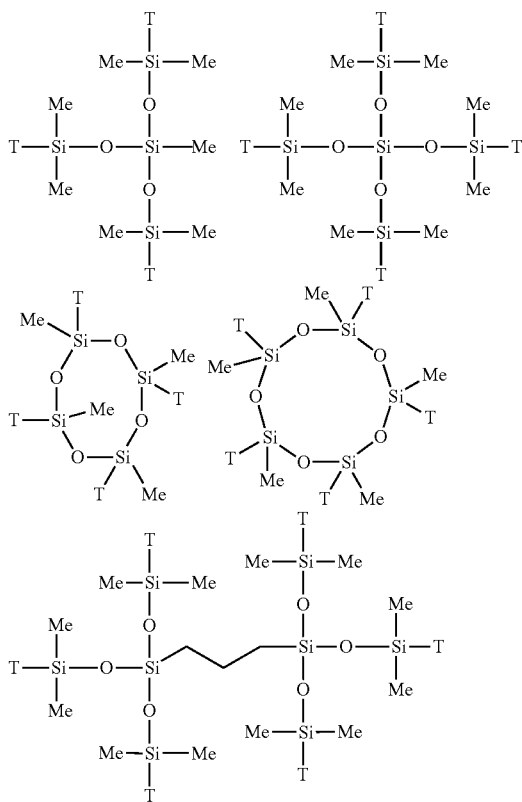

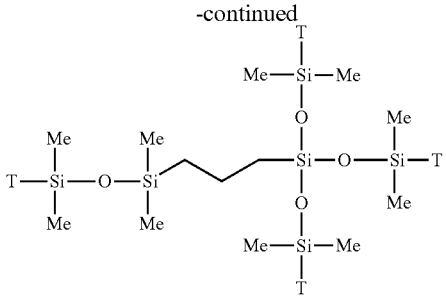

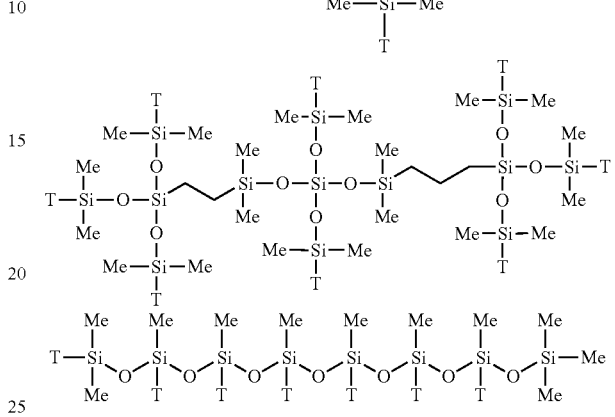

wherein, in each X group, any one of T is a following group which binds to A-Rf— of the main backbone of the formula (1a) and the formula (1b):
—CH$_2$O(CH$_2$)$_2$—,
—CH$_2$O(CH$_2$)$_3$—,
—CF$_2$O(CH$_2$)$_3$—,
—(CH$_2$)$_2$—,
—(CH$_2$)$_3$—,
—(CH$_2$)$_4$—,
—CONH—(CH$_2$)$_3$—,
—CON(CH$_3$)—(CH$_2$)$_3$—,
—CON(Ph)-(CH$_2$)$_3$— wherein Ph represents a phenyl group, or

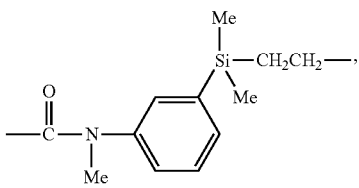

and
other one is —(CH$_2$)$_n$— wherein n is an integer of 2-6 which binds to a Si atom in the main backbone of the formula (1a) and the formula (1b),
the others are each independently a methyl group or a phenyl group.

In the above-mentioned formula (1a) and the formula (1b), Y represents a hydroxyl group, a hydrolyzable group, or a hydrocarbon group. The hydroxyl group may be, but is not particularly limited to, a group generated by hydrolysis of a hydrolyzable group.

The term "a hydrolyzable group" as used herein represents a group which can leave from the main backbone of a compound by a hydrolysis reaction. Examples of the hydrolyzable group include, but are not particularly limited to, —OR$^4$, —OCOR$^4$, —O—N=C(R$^4$)$_2$, —N(R$^4$)$_2$, —NHR$^4$, and a halogen atom wherein R$^4$ represents, each independently at each occurrence, a substituted or unsubstituted C$_{1-3}$ alkyl group.

The Y group is preferably a hydroxyl group, —O(R$^5$) wherein R$^5$ represents a C$_{1-12}$ alkyl group, preferably a C$_{1-6}$ alkyl group, more preferably a C$_{1-3}$ alkyl group, a C$_{1-12}$ alkyl group, a C$_{2-12}$ alkenyl group, a C$_{2-12}$ alkynyl group, or a phenyl group, more preferably —OCH$_3$, —OCH$_2$CH$_3$, or —OCH(CH$_3$)$_2$. These groups may be substituted by one or more substituents selected from, for example, a fluorine atom, a C$_{1-6}$ alkyl group, a C$_{2-6}$ alkenyl group, and a C$_{2-6}$alkynyl group.

In the above-mentioned formula (1a) and the formula (1b), Q represents —Z—SiR$^1_n$R$^2_{3-n}$.

Z represents, each independently at each occurrence, a divalent organic group.

Preferably, Z does not include a group which forms a siloxane bond together with a Si atom present in the end of the molecular backbone of the formula (1a) or the formula (1b), Z is preferably a C$_{1-6}$ alkylene group, —(CH$_2$)$_{s'}$—O—(CH$_2$)$_{t'}$— wherein s' is an integer of 1-6 and t' is an integer of 1-6 or -phenylene-(CH$_2$)$_{u'}$— wherein u' is an integer of 0-6, more preferably a C$_{1-3}$ alkylene group. These groups may be substituted by one or more substituents selected from, for example, a fluorine atom, a C$_{1-6}$ alkyl group, a C$_{2-6}$ alkenyl group, and a C$_{2-6}$ alkynyl group.

R$^1$ represents, each independently at each occurrence, a hydroxyl group or a hydrolyzable group. R$^1$ is preferably —OR$^6$ wherein R$^6$ represents a substituted or unsubstituted C$_{1-3}$ alkyl group, more preferably a methyl group.

R$^2$ represents, each independently at each occurrence, a C$_{1-22}$ alkyl group or Q'.

The above-mentioned Q' has the same definition as that of Q.

n is, each independently in each Q and Q', an integer of 0-3, and the total sum of n is 1 or more. In each Q or Q', when n is 0, Si in such Q or Q' does not have a hydroxyl group and a hydrolyzable group. Therefore, the total sum must be at least one.

In Q' present in the end of -Q-Q'$_{0-5}$ chain binding to a Si atom present in the end of the main backbone having a perfluoropolyether group, n is preferably 2, more preferably 3.

When at least one R$^2$ in Q is Q', there are two or more Si atoms which are linearly connected via the Z group in Q. The number of such Si atoms which are linearly connected via the Z group is up to five. It is noted that "the number of such Si atoms which are linearly connected via the Z group in Q" is equal to the repeating number of —Z—Si— which are linearly connected in Q.

For example, one example in which Si atoms are connected via the Z group in Q is shown below.

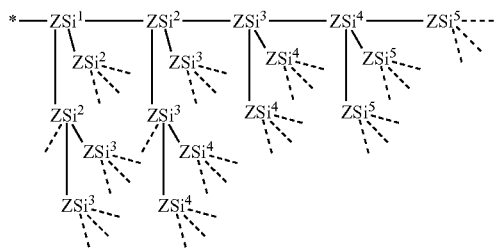

In the above formula, * represents a position binding to Si of the main backbone, and . . . represents that a predetermined group other than ZSi binds thereto, that is, when all three bonds of a Si atom are . . . , it means an end point of the repeat of Z. The number on the right shoulder of Si means the number of occurrences of Si which is linearly connected via the Z group from * In other words, in the chain in which the repeat of ZSi is completed at Si$^2$, "the number of such Si atoms which are linearly connected via the Z group in Q" is 2, similarly, in the chain in which the repeat of ZSi is completed at Si$^3$, Si$^4$ and Si$^5$, respectively, "the number of such Si atoms which are linearly connected via the Z group in Q" is 3, 4 and 5. It is noted that as seen from the above formula, there are some ZSi chains, but they need not have the same length and may be have each any length.

In a preferred embodiment of the present invention, as shown below, "the number of such Si atoms which are linearly connected via the Z group in Q" is 1 (left formula) or 2 (right formula) in all chains.

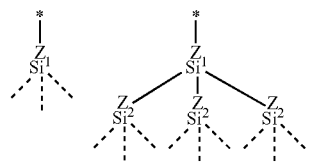

In one embodiment, the number of such Si atoms which are linearly connected via the Z group in Q is 1 (that is, there is only one Si in Q) or 2, preferably 1.

In the above-mentioned formula (1a) and the formula (1b), k is an integer selected from 1 to 3, preferably 2 or more, more preferably 3. By setting k at 3, the binding to the base material becomes strong, and it is possible to obtain high friction durability.

In one embodiment, the PFPE containing silane compound of the present invention is a compound of the formula (1a) or the formula (1b) wherein R$^2$ in Q is a C$_{1-22}$ alkyl group.

In one embodiment, the PFPE containing silane compound of the present invention is a compound of the formula (1a) or the formula (1b) wherein at least one of R$^2$ in Q is Q'.

In the above-mentioned PFPE containing silane compound of the formula (1a) or the formula (1b), an average molecular weight of the A-Rf— moiety is, but not particularly limited to, 500-30,000, preferably 1,500-30,000, more preferably 2,000-10,000.

The above-mentioned PFPE containing silane compound of the present invention of the formula (1a) or the formula (1b) has an average molecular weight of 5×10$^2$ to 1×10$^5$, but not particularly limited thereto. Among such range, it is preferable to have the average molecular weight of 2,000-30,000, more preferably 2,500-12,000, in view of friction durability. It is noted that the "average molecular weight" in the present invention means a number average molecular weight, and the "average molecular weight" is defined as a value measured by using $^{19}$F-NMR.

Next, the process for producing the PFPE containing silane compound of the present invention will be described.

The PFPE containing silane compound of the formula (1a) or the formula (1b) can be produced by using a method comprising the following steps:

Step (1): reacting a compound of the formula (1a-1) or the formula (1b-1):

A-Rf—X'—CH=CH$_2$ (1a-1)

CH$_2$=CH—X'—Rf—X'—CH=CH$_2$ (1b-1)

wherein A and Rf are as defined above, and X' represents a divalent organic group;
with HSiM₃ wherein M is each independently a halogen atom or a $C_{1-6}$ alkoxy group, to obtain a compound of the formula (1a-2) or the formula (1b-2):

A—Rf—X'—CH₂—CH₂—SiM₃ (1a-2)

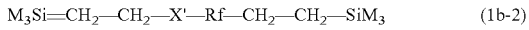
M₃Si—CH₂—CH₂—X'—Rf—CH₂—CH₂—SiM₃ (1b-2)

wherein A, Rf, X' and M are as defined above;

Step (2): reacting a compound of the formula (1a-2) or the formula (1b-2) with a compound of Formula: Hal-J-Z'—CH=CH₂ wherein Z' represents a bond or a linker, J represents Mg, Cu, Pd or Zn, and Hal represents a halogen atom, and optionally a compound of Formula: $Y_hL$ wherein Y is as defined above, L represents a group which is able to bind to Y, and h is an integer of 1-3, to obtain a compound of the formula (1a-3) or the formula (1b-3):

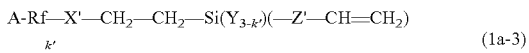
A-Rf—X'—CH₂—CH₂—Si(Y₃₋ₖ·)(—Z'—CH=CH₂)ₖ· (1a-3)

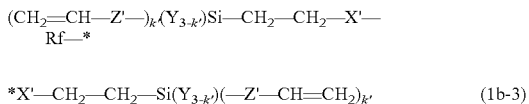
(CH₂=CH—Z'—)ₖ(Y₃₋ₖ·)Si—CH₂—CH₂—X'—Rf—*

*X'—CH₂—CH₂—Si(Y₃₋ₖ·)(—Z'—CH=CH₂)ₖ· (1b-3)

wherein A, Rf, X', Y and Z' are as defined above, and k' is an integer of 1-3; and Step (3): reacting a compound of the formula (1a-3) or the formula (1b-3) with HSiM₃ wherein M is, each independently, a halogen atom or a $C_{1-6}$ alkoxy group, and optionally
a compound of Formula: $R^1_iL'$ wherein $R^1$ is as defined above, L' represents a group which is able to bind to $R^1$, and i is an integer of 1-3, and/or
a compound of Formula: $R^{2'}_jL''$ wherein $R^{2'}$ represents a $C_{1-22}$ alkyl group, L'' represents a group which is able to bind to $R^{2'}$, and j is an integer of 1-3.

Alternatively, the step (2) may be substituted by the following step (2').

Step (2'):
reacting a compound of the formula (1a-2) or the formula (1b-2) with a compound of Formula: G-Z'—CH=CH₂ wherein Z' represents a bond or a divalent organic group, G represents Li, Na or K, and optionally,
a compound of Formula: $Y_hL$ wherein Y is as defined in claim 1, L represents a group which is able to bind to Y, and h is an integer of 1-3
to obtain a compound of the formula (1a-3) or the formula (1b-3):

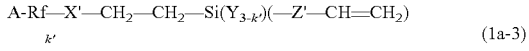
A-Rf—X'—CH₂—CH₂—Si(Y₃₋ₖ·)(—Z'—CH=CH₂)ₖ· (1a-3)

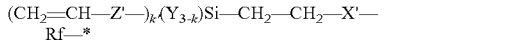
(CH₂=CH—Z'—)ₖ(Y₃₋ₖ·)Si—CH₂—CH₂—X'—Rf—*

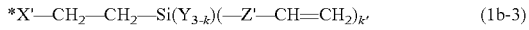
*X'—CH₂—CH₂—Si(Y₃₋ₖ·)(—Z'—CH=CH₂)ₖ· (1b-3)

wherein A, Rf, X', Y and Z' is as defined above, and k' is an integer of 1-3.

Hereinafter, the above-mentioned step (1) will be described in detail.

In Step (1), the compound of the formula (1a-1) or the formula (1b-1):

A-Rf—X'—CH=CH₂ (1a-1)

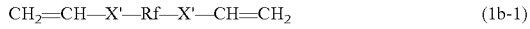
CH₂=CH—X'—Rf—X'—CH=CH₂ (1b-1)

is reacted with HSiM₃ to obtain the compound of the formula (1a-2) or the formula (1b-2):

A-Rf—X'—CH₂—CH₂—SiM₃ (1a-2)

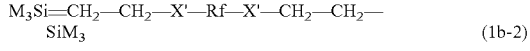
M₃Si—CH₂—CH₂—X'—Rf—X'—CH₂—CH₂—SiM₃ (1b-2)

In the above-mentioned formula (1a-1) or the formula (1b-1), A and Rf are as defined in the formula (1a) and the formula (1b) mentioned above.

In the above-mentioned formula (1a-1) or the formula (1b-1), X' represents a divalent organic group. It is noted that X'—CH₂CH₂— corresponds to X in the formula (1a) and the formula (1b) mentioned above.

The compound of the formula (1a-1) or the formula (1b-1) is commercially available, or can be produced from a commercially available compound by using a common technique in the art.

In HSiM₃ used in Step (1), M is each independently a halogen atom (for example, I, Br, Cl, F, or the like) or a $C_{1-6}$ alkoxy group, preferably a halogen atom, more preferably Cl. The compound is commercially available, or can be produced from a commercially available compound by using a common technique in the art.

An amount of HSiM₃ is preferably 1 mole or more with respect to 1 mole of a terminal —CH=CH₂ group of the total amount of the compound of the formula (1a-1) and/or the formula (1b-1) (when two or more compounds are used, as the total thereof; hereinafter the same shall apply).

It is preferable that a reaction of Step (1) is conducted in the presence of a suitable catalyst in a suitable solvent.

Examples of the suitable catalyst include, but are not particularly limited to, for example, Pt, Pd, Rh, and the like. The catalyst may be in the form of any form, for example, a complex form.

Examples of the suitable solvent are not limited as long as it is a solvent which does not adversely influence the reaction, and include, for example, 1,3-bis(trifluoromethyl)benzene, perfluorobuthyl ethyl ether, perfluorohexyl methyl ether, and the like.

A reaction temperature in the reaction is not particularly limited to, but is usually 0 to 100° C., preferably 50 to 80° C. The reaction time is not particularly limited to, but is usually 60 to 600 minutes, preferably 120 to 240 minutes. The reaction pressure is not particularly limited to, but is −0.2 to 1 MPa (gauge pressure), conveniently an ambient pressure.

Hereinafter, the above-mentioned step (2) will be described in detail.

In Step (2), the compound of the formula (1a-2) or the formula (1b-2) obtained in Step (1) is reacted with a compound of Formula: Hal-J-Z'—CH=CH₂, and optionally
a compound of Formula: $Y_hL$
to obtain a compound of the formula (1a-3) or the formula (1b-3):

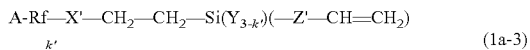
A-Rf—X'—CH₂—CH₂—Si(Y₃₋ₖ·)(—Z'—CH=CH₂)ₖ· (1a-3)

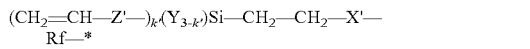
(CH₂=CH—Z'—)ₖ(Y₃₋ₖ·)Si—CH₂—CH₂—X'—Rf—*

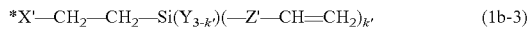
*X'—CH₂—CH₂—Si(Y₃₋ₖ·)(—Z'—CH=CH₂)ₖ· (1b-3)

In the above-mentioned formula: Hal-J-Z'—CH=CH₂ in Step (2), Hal represents a halogen atom (for example, I, Br, Cl, F, and the like), J represents Mg, Cu, Pd or Zn, and Z' represents a bond or a divalent organic group. The "divalent organic group" has the same definition as that of "the divalent organic group" in Z in the above-mentioned formula (1a) and the formula (1b). It is noted that the Z'—CH₂CH₂— group corresponds to Z in the formula (1a) and the formula (1b).

The compound of the formula: Hal-J-Z'—CH=CH₂ is preferably a compound wherein J is Mg. This compound is known as a Grignard reagent in the art and is commercially available, or can be produced from a commercially available compound by using a common technique in the art.

An amount of the compound of Hal-J-Z'—CH=CH₂ used in Step (2) is not particularly limited to, but is preferably 2 moles or more, more preferably 2-4 moles with respect to 1 mole of a terminal SiCl₃ group of the compound of the formula (1a-2) and/or the formula (1b-2). It will be understood that the amount can be changed depending on the amount used of the compound of $Y_hL$ described below.

In the above-mentioned formula: $Y_hL$ in Step (2), Y is as defined in the above-mentioned formula (1a) and the formula (1b), L represents a group which is able to bind to Y and h is an integer of 1-3. The "group which is able to bind to Y" is not limited as long as it can bind to Y and Y can leave from it in the above reaction, and includes, for example, a hydrogen atom, lithium, sodium, and the like. The group which is able to bind to Y may be a group which can have a plurality of Y groups, for example, CH₂ or CH. In this case, the compound of $Y_hL$ may be CH₂Y₂ and CHY₃, respectively. Those skilled in the art can select a suitable group which is able to bind to Y depending on the type of compound to be reacted, or a condition such as a solvent to be used and a temperature.

In Step (2), when the compound of $Y_hL$ is used, the amount used can be changed depending on the amount of Y group to be introduced, and such amount can be appropriately determined by those skilled in the art.

In the reaction, the compound of the formula: Hal-J-Z'—CH=CH₂ and the compound of the formula: $Y_hL$ may be simultaneously reacted, or the two step reaction is conducted in which one compound is firstly reacted and then the other compound is reacted. Those skilled in the art can appropriately decide whether both compounds are simultaneously reacted, or either compound is firstly reacted in the sequential reaction.

It is preferable that the reaction of Step (2) is conducted in the presence of a suitable catalyst in a suitable solvent.

Examples of the suitable catalyst include, but are not particularly limited to, for example, Zn, Cu, Fe, and the like. The catalyst may be in the form of any form, for example, a complex form.

Examples of the suitable solvent are not particularly limited as long as it is a solvent which does not adversely influence the reaction, and include, for example, 1,3-bis(trifluoromethyl)benzene, perfluorobuthyl ethyl ether, perfluorohexyl methyl ether, and the like.

A reaction temperature in the reaction is not particularly limited to, but is usually −78 to 150° C., preferably −20 to 30° C. The reaction time is not particularly limited to, but is usually 60 to 720 minutes, preferably 120 to 240 minutes. The reaction pressure is not particularly limited to, but is −0.2 to 1 MPa (gauge pressure), conveniently an ambient pressure.

Hereinafter, the above-mentioned step (2') will be described in detail.

In Step (2'), the compound of the above-mentioned formula (1a-2) or the formula (1b-2) is reacted with the compound of
Formula: G-Z'—CH=CH₂, and optionally
a compound of
Formula: $Y_hL$
to obtain the compound of the formula (1a-3) or the formula (1b-3):

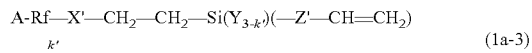

(1a-3)

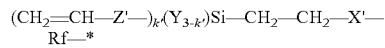

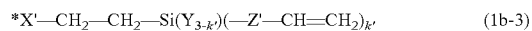

(1b-3)

The Step (2') can be understood to be a reaction in which G-Z'—CH=CH₂ is used in place of Hal-J-Z'—CH=CH₂ in Step (2).

In G-Z'—CH=CH₂, Z' represents a bond or a divalent organic group, and G represents Li, Na or K. The "divalent organic group" has the same definition as that of "the divalent organic group" in Z in the above-mentioned formula (1a) and the formula (1b). It is noted that the Z'—CH₂CH₂— group corresponds to Z in the above-mentioned formula (1a) and the formula (1b).

An amount of the compound of G-Z'—CH=CH₂ used in Step (2') is not particularly limited to, but is preferably 2 moles or more, more preferably 2-4 moles with respect to 1 mole of a terminal SiCl₃ group of the compound of the formula (1a-2) and/or the formula (1b-2). It will be understood that the amount can be changed depending on the amount used of the compound of $Y_hL$ described below.

The formula: $Y_hL$ in Step (2') has the same definition as that of the formula: $Y_hL$ in Step (2).

In Step (2'), when the compound of $Y_hL$ is used, the amount used can be changed depending on the amount of Y group to be introduced, and such amount can be appropriately determined by those skilled in the art.

In the reaction, the compound of the formula: G-Z'—CH=CH₂ and the compound of the formula: $Y_hL$ may be simultaneously reacted, or the two step reaction is conducted in which one compound is firstly reacted and then the other compound is reacted. Those skilled in the art can appropriately decide whether both compounds are simultaneously reacted, or either compound is firstly reacted in the sequential reaction.

It is preferable that a reaction of Step (2') is conducted in the presence of a suitable catalyst in a suitable solvent.

Examples of the suitable catalyst include, but are not particularly limited to, for example, Zn, Cu, Fe, and the like. The catalyst may be in the form of any form, for example, a complex form.

Examples of the suitable solvent are not particularly limited as long as it is a solvent which does not adversely influence the reaction, and include, for example, 1,3-bis(trifluoromethyl)benzene, perfluorobuthyl ethyl ether, perfluorohexyl methyl ether, and the like.

A reaction temperature in the reaction is not particularly limited to, but is usually −78 to 150° C., preferably −20 to 30° C. The reaction time is not particularly limited to, but is usually 60 to 720 minutes, preferably 120 to 240 minutes. The reaction pressure is not particularly limited to, but is −0.2 to 1 MPa (gauge pressure), conveniently an ambient pressure.

Hereinafter, the above-mentioned step (3) will be described in detail.

In Step (3), the compound of the formula (1a-3) or the formula (1b-3) obtained in the above-mentioned Step (2) is reacted with $HSiM_3$ wherein M is as defined above, preferably a halogen atom, more preferably Cl, and optionally, the compound of the formula: $R^1{}_iL'$ and/or the compound of the formula: $R^{2'}{}_jL''$.

In the formula: $R^1{}_iL'$ in Step (3), $R^1$ has the same definition as that of the above-mentioned formula (1a) and the formula (1b), L' represents a group which is able to bind to R', and i is an integer of 1-3.

In the formula: $R^{2'}{}_jL''$ in Step (3), $R^{2'}$ represents a $C_{2-22}$ alkyl group, L" represents a group which is able to bind to $R^{2'}$, and j is an integer of 1-3.

The "group which is able to bind to $R^1$" and the "group which is able to bind to $R^{2'}$" which are represented by L' and L", respectively, is not limited as long as it can bind to $R^2$ and $R^{2'}$ respectively, and $R^2$ and $R^{2'}$ can leave from these groups in the above reaction, and may be for example the same group as the above-mentioned L. Those skilled in the art can select a suitable group which is able to bind to $R^2$ and a suitable group which is able to bind to $R^{2'}$ depending on the type of compound to be reacted, or a condition such as a solvent to be used and a temperature.

An amount of $HSiM_3$ used in Step (3) is preferably 1 mole or more, preferably 2 moles with respect to 1 mole of a terminal —CH=$CH_2$ group in the above-mentioned compound of the formula (1a-3) and/or the formula (1b-3).

In Step (3), when the compound of $R^1{}_iL'$ is used, the amount used can be changed depending on the amount of $R^2$ group to be introduced, and such amount can be appropriately determined by those skilled in the art.

In Step (3), when the compound of $R^{2'}{}_jL''$ is used, the amount used can be changed depending on the amount of $R^2$ group to be introduced, and such amount can be appropriately determined by those skilled in the art.

In a reaction of Step (3), firstly, the terminal —CH=$CH_2$ group of the compound of the formula (1a-3) and/or the formula (1b-3) is reacted with and $HSiM_3$ to convert its terminal to a —$CH_2CH_2SiM_3$ group. When all of the terminal —CH=$CH_2$ groups are converted to the —$CH_2CH_2SiM_3$ group, k' in the formula (1a-2) or the formula (1b-2) is equal to k in the formula (1a) or the formula (1b). Then, this terminal —$CH_2CH_2SiM_3$ group is reacted with the compound of $R^1{}_iL'$ and/or the compound of $R^{2'}{}_jL''$ to substitute M with $R^2$ or $R^{2'}$. It is noted that the compound of $R^1{}_iL'$ and the compound of $R^{2'}{}_jL''$ may be simultaneously or separately reacted.

However, in one embodiment of the present invention, $HSiM_3$, the compound of $R^1{}_iL'$ and the compound of $R^{2'}{}_jL''$ can be used as a compound of $HSi(R^1{}_i)(R^{2'}{}_j)$ (in this case, i+j is 3). Those skilled in the art can produce the compound of $HSi(R^1{}_i)(R^{2'}{}_j)$ by using a common technique in the art.

In another embodiment, the sum of the amounts used of the compound of $R^1{}_iL'$ and/or the compound of $R^{2'}{}_jL''$ in Step (3) is 3 moles or more with respect to 1 mole of a terminal —CH=$CH_2$ group in compound of the formula (1a-3) and/or the formula (1b-3). According to such embodiment, substantially all M of the terminal —$CH_2CH_2SiM_3$ produced in Step (3) can be substituted by $R^1$ or $R^{2'}$. That is, the compound wherein the number of Si atoms which are straightly linked via the Z group in Q is 1 can be obtained.

In further embodiment, the sum of the amounts used of the compound of $R^1{}_iL'$ and/or the compound of $R^{2'}{}_jL''$ in Step (3) is 3 moles or less with respect to 1 mole of a terminal —CH=$CH_2$ group in compound of the formula (1a-3) and/or the formula (1b-3). According to such embodiment, some or all M of the terminal —$CH_2CH_2SiM_3$ produced in Step (3) cannot be substituted by $R^1$ or $R^{2'}$ and can remain. Such remaining Si-M portion is reacted with a compound of the formula: Hal-J-Z'—CH=$CH_2$ wherein Hal represents a halogen atom, J represents Mg, Cu or Zn, and Z' is a bond or a divalent organic group similarly to Step (2) to convert the terminal portion to —CH=$CH_2$, thereby allowing the compound to be subjected to the same reaction as the reaction of Step (3). By repeating the reactions, Si atoms can be connected via Z group in a tree shape at the end of the compound of the formula (1a) or the formula (1b).

It is preferable that a reaction of Step (3) is conducted in the presence of a suitable catalyst in a suitable solvent.

Examples of the suitable catalyst include, but are not particularly limited to, for example, Pt, Pd, Rh, and the like. The catalyst may be in the form of any form, for example, a complex form.

It is preferable that the reactions of Step (1) and (3) are conducted in the presence of a suitable rearrangement preventing agent.

Examples of the suitable rearrangement preventing agent include, but are not particularly limited to, a carboxylic acid compound. The carboxylic acid compound may comprise (a) carboxylic acid, (b) an anhydride of a carboxylic acid, (c) a silylated carboxylic acid, and/or (d) a substance that will produce the above-mentioned carboxylic acid compounds (i.e., (a), (b), and/or (c)) in the reaction of Step (3). These carboxylic acid compounds may be used alone or in combination of two or more.

When the rearrangement preventing agent comprises (a) carboxylic acid, any carboxylic acid having a carboxyl group may be used. Suitable examples of the carboxylic acid include, but are not particularly limited to, a saturated carboxylic acid, an unsaturated carboxylic acid, a monocarboxylic acid, and a dicarboxylic acid. Specific examples of the suitable carboxylic acid include, but are not particularly limited to, a saturated monocarboxylic acid such as formic acid, acetic acid, propionic acid, n-butyric acid, isobutyric acid, hexanoic acid, cyclohexanoic acid, lauric acid, and stearic acid; a saturated dicarboxylic acid such as oxalic acid and adipic acid; an aromatic carboxylic acid such as benzoic acid and para-phthalic acid; a carboxylic acid in which the hydrogen atom of the hydrocarbon group of these carboxylic acids has been substituted with a halogen atom or an organosilyl group, such as chloroacetic acid, dichloroacetic acid, trifluoroacetic acid, para-chlorobenzoic acid, and trimethylsilylacetic acid; an unsaturated fatty acid such as acrylic acid, methacrylic acid, and oleic acid; and compounds having a hydroxy group, a carbonyl group or an amino group in addition to the carboxyl group, namely, a hydroxy acid such as lactic acid, a keto acid such as acetoacetic acid, an aldehyde acid such as glyoxylic acid, and an amino acid such as glutamic acid.

Examples of (b) the anhydride of a carboxylic acid include, but are not particularly limited to, acetic anhydride, propionic anhydride, and benzoic anhydride. These anhydrides of a carboxylic acid may be produced in the reaction system of Step (3), and include acetyl chloride, butyryl chloride, benzoyl chloride, and other carboxylic acid halides; a carboxylic acid metal salt such as zinc acetate and thallium acetate, and a carboxylic ester that are decomposed by light or heat, such as (2-nitrobenzyl)propionate.

Examples of (c) the silylated carboxylic acid include, but are not particularly limited to, trialkylsilylated carboxylic acids, such as trimethylsilyl formate, trimethylsilyl acetate, triethylsilyl propionate, trimethylsilyl benzoate, and trimethylsilyl trifluoroacetate; and di-, tri-, or tetracarboxysilylates, such as dimethyldiacetoxysilane, diphenyldiacetoxysilane, methyltriacetoxysilane, ethyltriacetoxysilane, vinyltriacetoxysilane, di-t-butoxydiacetoxysilane, and silicon tetrabenzoate.

The rearrangement preventing agent is used in an amount of 0.001-20 weight %, for example 0.01-5 weight %, or 0.01-1 weight %, but not particularly limited thereto. Those skilled in the art can select the amount of using the rearrangement preventing agent depending on the compound to be reacted, an agent, a solvent, and other conditions. The rearrangement preventing agent is commercially available as DOW CORNING (registered trademark) ETS 900 or XIAMETER (registered trademark) OFS-1579 Silane available from Dow Corning Corporation of Midland, Mich.

Examples of the suitable solvent are not limited as long as it is a solvent which does not adversely influence the reaction, and include for example 1,3-bis(trifluoromethyl) benzene, perfluorobuthyl ethyl ether, perfluorohexyl methyl ether, and the like.

A reaction temperature in the reaction is not particularly limited to, but is usually 0 to 100° C., preferably 50 to 80° C. The reaction time is not particularly limited to, but is usually 30 to 600 minutes, preferably 60 to 240 minutes. The reaction pressure is not particularly limited to, but is −0.2 to 1 MPa (gauge pressure), conveniently an ambient pressure.

Also, the present invention provides a compound of the formula (1a-3') or the formula (1b-3'), that is, an intermediate for the above-mentioned method for producing:

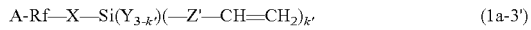  (1a-3')

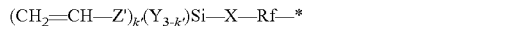

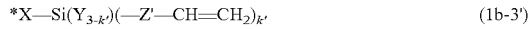  (1b-3')

wherein A represents a $C_{1-16}$ alkyl which may be substituted by one or more fluorine atoms;

Rf represents $-(OC_4F_8)_a-(OC_3F_6)_b-(OC_2F_4)_c-(OCF_2)_d-$ wherein a, b, c and d are each independently an integer of 0 or more and 200 or less, the sum of a, b, c and d is 1 or more, and the occurrence order of the respective repeating units in parentheses with the subscript a, b, c or d is not limited in the formula;

X represents a divalent organic group;

Y represents a hydroxyl group, a hydrolyzable group, or a hydrocarbon group; and Z' is a bond or a divalent organic group.

Furthermore, the present invention provides a process for producing the compound of the formula (1a-3') or the formula (1b-3') which comprises a step of reacting a compound of the formula (1a-2') or the formula (1b-2'):

  (1a-2')

  (1b-2')

wherein A, Rf, and X are as defined above, M is a halogen atom or a $C_{2-6}$ alkoxy group, with a compound of Formula: Hal-J-Z'—CH=CH$_2$ wherein Z' is as defined above, J represents Mg, Cu, Pd or Zn, and Hal represents a halogen atom, and optionally a compound of Formula: Y$_h$L wherein Y is as defined above, L represents a group which is able to bind to Y, and h is an integer of 1-3. Such process corresponds to the above-mentioned Step (2) in the process for producing the PFPE containing silane compound of the present invention.

Next, the surface-treating agent of the present invention will be described.

The surface-treating agent of the present invention comprises at least one the perfluoro(poly)ether group containing silane compound of the formula (1a) and/or the formula (1b).

The surface-treating agent of the present invention can provide a base material with water-repellency, oil-repellency, antifouling property and friction durability, and can be suitably used as an antifouling-coating agent, although the present invention is not particularly limited thereto.

In one embodiment, the surface-treating agent of the present invention comprises at least one compound of the formula (1a) and/or the formula (1b) wherein k is 3.

In one embodiment, the surface-treating agent of the present invention comprises at least one compound of the formula (1a) and/or the formula (1b) wherein the number of Si atoms which are straightly linked via the Z group in Q is 1 or 2.

In one embodiment, the surface-treating agent of the present invention comprises at least one compound of the formula (1a) and/or the formula (1b) wherein A is a $C_{1-16}$ perfluoroalkyl group.

In one embodiment, the surface-treating agent of the present invention comprises at least one compound of the formula (1a) and/or the formula (1b) wherein $R^2$ in Q is a $C_{1-22}$ alkyl group.

In another embodiment, the surface-treating agent of the present invention comprises two or more perfluoro(poly) ether group containing silane compounds of the formula (1a) and/or the formula (1b). In this case, an average of all k of the compounds may be 1 or more and 3 or less, for example, 2 or more and 3 or less, preferably 3.

In further another embodiment, the surface-treating agent of the present invention comprises one or more perfluoro (poly)ether group containing silane compounds of the formula (1a) and/or the formula (1b) wherein $R^2$ in Q is a $C_{1-22}$ alkyl group, and k is 3. In such embodiment, the perfluoro (poly)ether group containing silane compound comprised in the surface-treating agent of the present invention may be one or more compounds of the formula (1a).

The above-mentioned average of k means an average value of k in each PFPE containing silane compound of the formula (1a) and the formula (1b) comprised in the surface-treating agent (a compound of the formula (1b) has k at both terminals, that is, has two k). Such average can be measured, for example, by using Si-NMR. Alternatively, the average can be measured by using H-NMR. The measure can be easily conducted by those skilled in the art. For example, in the case that a plurality of compounds of the following formula:

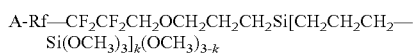

having different value of k as a mixture are contained in the surface-treating agent, when the measure is conducted by using Si-NMR, the average can be measured by obtaining the Si-NMR spectrum of such mixture and calculating the ratio of peak areas of Si. Alternatively, when the measure is conducted by using H-NMR, the average can be measured by obtaining the H-NMR spectrum of such mixture and calculating the ratio of hydrogen atoms bonding to CH$_2$OCH$_2$ and hydrogen atoms bonding to Si—CH$_2$CH$_2$CH$_2$—Si.

The above-mentioned surface-treating agent may comprise other components in addition to the compound of the formula (1a) and/or the formula (1b). Examples of the other components include, but are not particularly limited to, for example, a (non-reactive) fluoropolyether compound which may be also understood as a fluorine-containing oil, preferably a perfluoro(poly)ether compound (hereinafter, referred to as "the fluorine-containing oil"), a (non-reactive) silicone compound which may be also understood as a silicone oil (hereinafter referred to as "a silicone oil"), a catalyst, and the like.

Examples of the above-mentioned fluorine-containing oil include, but are not particularly limited to, for example, a compound of the following general formula (3) (a perfluoro (poly)ether compound).

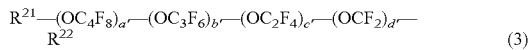
(3)

Wherein, $R^{21}$ represents an alkyl group having 1-16 carbon atoms which may be substituted by one or more fluorine atoms (preferably, a perfluoroalkyl group having 1-16 carbon atoms), $R^{22}$ represents an alkyl group having 1-carbon atoms which may be substituted by one or more fluorine atoms (preferably, a perfluoroalkyl group having 1-16 carbon atoms), a fluorine atom or a hydrogen atom, and more preferably, $R^{21}$ and $R^{22}$ is each independently a perfluoroalkyl group having 1-3 carbon atoms.

Subscripts a', b', c' and d' represent the repeating number of each of four repeating units of perfluoropolyether which constitute a main backbone of the polymer, and are each independently an integer of 0 or more and 300 or less, and the sum of a', b', c' and d' is at least 1, preferably 1-300, more preferably 20-300. The occurrence order of the respective repeating units in parentheses with the subscript a', b', c' or d' is not limited in the formulae. Among these repeating units, the $-(OC_4F_8)-$ group may be any of $-(OCF_2CF_2CF_2CF_2)-$, $-(OCF(CF_3)CF_2CF_2)-$, $-(OCF_2CF(CF_3)CF_2)-$, $-(OCF_2CF_2CF(CF_3))-$, $-(OC(CF_3)_2CF_2)-$, $-(OCF_2C(CF_3)_2)-$, $-(OCF(CF_3)CF(CF_3))-$, $-(OCF(C_2F_5)CF_2)-$ and $-(OCF_2CF(C_2F_5))-$, preferably $-(OCF_2CF_2CF_2CF_2)-$. The $-(OC_3F_6)-$ group may be any of $-(OCF_2CF_2CF_2)-$, $-(OCF(CF_3)CF_2)-$ and $-(OCF_2CF(CF_3))-$, preferably $-(OCF_2CF_2CF_2)-$. The $-(OC_2F_4)-$ group may be any of $-(OCF_2CF_2)-$ and $-(OCF(CF_3))-$, preferably $-(OCF_2CF_2)-$.

Examples of the perfluoropolyether compound of the above general formula (3) include a compound of any of the following general formulae (3a) and (3b) (may be one compound or a mixture of two or more compounds).

(3a)

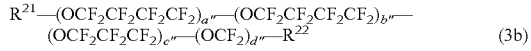
(3b)

In these formulae:

$R^{21}$ and $R^{22}$ are as defined above; in the formula (3a), b" is an integer of 1 or more and 100 or less; and in the formula (3b), a" and b" are each independently an integer of 1 or more and 30 or less, and c" and d" are each independently an integer of 1 or more and 300 or less. The occurrence order of the respective repeating units in parentheses with the subscript a", b", c" or d" is not limited in the formulae.

The above-mentioned fluorine-containing oil may have an average molecular weight of 1,000-30,000. By having such average molecular weight, high surface slip property can be obtained.

The fluorine-containing oil may be contained in the surface-treating agent of the present invention, for example, at 0-500 parts by mass, preferably 0-400 parts by mass, more preferably 25-400 parts by mass with respect to 100 parts by mass of the PFPE containing silane compound of the present invention (as the total mass when two or more compounds are used; hereinafter the same shall apply).

The compound of the general formula (3a) and the compound of the general formula (3b) may be used alone or in combination. The compound of the general formula (3b) is preferable than the compound of the general formula (3a) since the compound of the general formula (3b) provides higher surface slip property than the compound of the general formula (3a). When they are used in combination, the ratio by mass of the compound of the general formula (3a) to the compound of the general formula (3b) is preferably 1:1 to 1:30, more preferably 1:1 to 1:10. By applying such ratio by mass, a perfluoropolyether group-containing silane-based coating which provides a good balance of surface slip property and friction durability can be obtained.

In one embodiment, the fluorine-containing oil comprises one or more compounds of the general formula (3b). In such embodiment, the mass ratio of the compound of the formula (1a) and the formula (1b) to the compound of the formula (3b) in the surface-treating agent is preferably 4:1 to 1:4.

In one preferable embodiment, the surface-treating agent of the present invention comprises the compound of the formula (1a) or the formula (1b) wherein Rf is $-(OCF_2CF_2CF_2)_b-$ (b is an integer of 1-200) and the compound of the formula (3b). By forming a surface-treating layer by using such surface-treating agent with a wet coating method or a vacuum deposition method, preferably vacuum deposition, excellent friction durability and surface slip property can be obtained.

In one preferable embodiment, the surface-treating agent of the present invention comprises the compound wherein Rf represents $-(OC_4F_8)_a-(OC_3F_6)_b-(OC_2F_4)_c-(OCF_2)_d-$ wherein a and b are each independently an integer of 0 or more and 30 or less, preferably 0 or more and 10 or less, and c and d are each independently an integer of 1 or more and 200 or less, and the sum of a, b, c and d is an integer of 10 or more and 200 or less. The occurrence order of the respective repeating units in parentheses with the subscript a, b, c or d is not limited in the formula and the compound of the formula (3b). By forming a surface-treating layer by using such surface-treating agent with a wet coating method or a vacuum deposition method, preferably vacuum deposition, more excellent friction durability and surface slip property can be obtained.

In these embodiments, an average molecular weight of the compound of the formula (3a) is preferably 2,000-8,000.

In these embodiments, an average molecular weight of the compound of the formula (3b) is preferably 8,000-30,000 when a surface-treating layer is formed by a dry coating method, for example, vacuum deposition, and is preferably 2,000-10,000, in particular 3,000-5,000 when a surface-treating layer is formed by using a wet coating method, for example, spray coating.

In a preferable embodiment, when a surface-treating layer is formed by using vacuum deposition, an average molecular weight of the fluorine-containing oil may be higher than an average molecular weight of the compound of the formula (1a) or the formula (1b). By selecting such average molecular weights of the compound of the formula (1a) or the formula (1b) and the fluorine-containing oil, more excellent friction durability and surface slip property can be obtained.

From the other point of view, the fluorine-containing oil may be a compound of the general formula A'-F wherein A' is a $C_{5-16}$ perfluoroalkyl group. The compound of A'-F is preferable because the compound has high affinity for the compound of the formula (1a) and the formula (1b).

The fluorine-containing oil contributes to increasing of surface slip property of the surface-treating layer.

Examples of the above-mentioned silicone oil include, for example, a liner or cyclic silicone oil having 2,000 or less siloxane bonds. The liner silicone oil may be so-called a straight silicone oil and a modified silicon oil. Examples of the straight silicone oil include dimethylsilicone oil, methylphenylsilicone oil, and methylhydrogensilicone oil. Examples of the modified silicone oil include that which is obtained by modifying a straight silicone oil with alkyl, aralkyl, polyether, higher fatty acid ester, fluoroalkyl, amino, epoxy, carboxyl, alcohol, or the like. Examples of the cyclic silicone oil include, for example, cyclic dimethylsiloxane oil.

The silicone oil may be contained in the surface-treating agent of the present invention, for example, at 0-300 parts by mass, preferably 50-200 parts by mass with respect to 100 parts by mass of the PFPE containing silane compound of the present invention (as the total mass when two or more compounds are used; hereinafter the same shall apply).

The silicone oil contributes to increasing of surface slip property of the surface-treating layer.

Examples of the above-mentioned catalyst include an acid (for example, acetic acid, trifluoroacetic acid, etc.), a base (for example, ammonia, triethylamine, diethylamine, etc.), a transition metal (for example, Ti, Ni, Sn, etc.), and the like.

The catalyst facilitates hydrolysis and dehydration-condensation of the PFPE containing silane compound of the present invention to facilitate a formation of the surface-treating layer.

Examples of the other components other than the above-mentioned components include, for example, tetraethoxysilane, methyltrimethoxysilane, 3-aminopropyltrimethoxysilane, 3-glycidoxypropyltrimethoxysilane, methyltriacetoxysilane, and the like.

The surface-treating agent of the present invention is impregnated into a porous material, for example, a porous ceramic material, a metal fiber for example that obtained by solidifying a steel wool to obtain a pellet. The pellet can be used, for example, in vacuum deposition.

Next, the article of the present invention will be described.

The article of the present invention comprises a base material and a layer (surface-treating layer) which is formed from the PFPE containing silane compound or the surface-treating agent of the present invention (hereinafter, referred to simply as "surface-treating agent" as a representative thereof) on the surface of the base material. This article can be produced, for example, as follows.

Firstly, the base material is provided. The base material usable in the present invention may be composed of any suitable material such as a glass, a resin (may be a natural or synthetic resin such as a common plastic material, and may be in form of a plate, a film, or others), a metal (may be a simple substance of a metal such as aluminum, copper, or iron, or a complex such as alloy or the like), a ceramic, a semiconductor (silicon, germanium, or the like), a fiber (a fabric, a non-woven fabric, or the like), a fur, a leather, a wood, a pottery, a stone, an architectural member or the like.

For example, when an article to be produced is an optical member, a material constituting the surface of the base material may be a material for an optical member, for example, a glass or a transparent plastic. For example, when an article to be produced is an optical member, any layer (or film) such as a hard coating layer or an antireflection layer may be formed on the surface (outermost layer) of the base material. As the antireflection layer, either a single antireflection layer or a multi antireflection layer may be used. Examples of an inorganic material usable in the antireflection layer include $SiO_2$, $SiO$, $ZrO_2$, $TiO_2$, $TiO$, $Ti_2O_3$, $Tl_2O_5$, $Al_2O_3$, $Ta_2O_5$, $CeO_2$, $MgO$, $Y_2O_3$, $SnO_2$, $MgF_2$, $WO_3$, and the Like. These inorganic materials may be used alone or in combination with two or more (for example, as a mixture). When multi antireflection layer is formed, preferably, $SiO_2$ and/or $SiO$ are used in the outermost layer. When an article to be produced is an optical glass part for a touch panel, it may have a transparent electrode, for example, a thin layer comprising indium tin oxide (ITO), indium zinc oxide, or the like on a part of the surface of the base material (glass). Furthermore, the base material may have an insulating layer, an adhesive layer, a protecting layer, a decorated frame layer (I-CON), an atomizing layer, a hard coating layer, a polarizing film, a phase difference film, a liquid crystal display module, and the like, depending on its specific specification.

The shape of the base material is not specifically limited. The region of the surface of the base material on which the surface-treating layer should be formed may be at least a part of the surface of the base material, and may be appropriately determined depending on use, the specific specification, and the like of the article to be produced.

The base material may be that of which at least the surface consists of a material originally having a hydroxyl group. Examples of such material include a glass, in addition, a metal on which a natural oxidized film or a thermal oxidized film is formed (in particular, a base metal), a ceramic, a semiconductor, and the like. Alternatively, as in a resin, when the hydroxyl groups are present but not sufficient, or when the hydroxyl group is originally absent, the hydroxyl group can be introduced on the surface of the base material, or the number of the hydroxyl group can be increased by subjecting the base material to any pretreatment. Examples of the pretreatment include a plasma treatment (for example, corona discharge) or an ion beam irradiation. The plasma treatment may be suitably used to introduce the hydroxyl group into or increase it on the surface of the base material, further, to clarify the surface of the base material (remove foreign materials, and the like). Alternatively, other examples of the pretreatment include a method wherein a monolayer of a surface adsorbent having a carbon-carbon unsaturated bond group is formed on the surface of the base material by using a LB method (Langmuir-Blodgett method) or a chemical adsorption method beforehand, and then, cleaving the unsaturated bond under an atmosphere of oxygen and nitrogen.

Alternatively, the base material may be that of which at least the surface consists of a material comprising other reactive group such as a silicon compound having one or more Si—H groups or alkoxysilane.

Next, the film of the above surface-treating agent of the present invention is formed on the surface of the base material, and the film is post-treated, as necessary, and thereby the surface-treating layer is formed from the surface-treating agent.

The formation of the film of the surface-treating agent of the present invention can be performed by applying the above surface-treating agent on the surface of the base material such that the surface-treating agent coats the surface. The method of coating is not specifically limited. For example, a wet coating method or a dry coating method can be used.

Examples of the wet coating method include dip coating, spin coating, flow coating, spray coating, roll coating, gravure coating, and a similar method.

Examples of the dry coating method include deposition (usually, vacuum deposition), sputtering, CVD and a similar method. The specific examples of the deposition method (usually, vacuum deposition) include resistance heating, electron beam, high-frequency heating using microwave, etc., ion beam, and a similar method. The specific examples of the CVD method include plasma-CVD, optical CVD, thermal CVD and a similar method. The deposition method is will be described below in more detail.

Additionally, coating can be performed by an atmospheric pressure plasma method.

When the wet coating method is used, the surface-treating agent of the present invention is diluted with a solvent, and then it is applied to the surface of the base material. In view of stability of the surface-treating agent of the present invention and volatile property of the solvent, the following solvents are preferably used: an aliphatic perfluorohydrocarbon having 5-12 carbon atoms (for example, perfluorohexane, perfluoromethylcyclohexane and perfluoro-1,3-dimethylcyclohexane); an aromatic polyfluorohydrocarbon (for example, bis(trifluoromethyl)benzene); an aliphatic polyfluorohydrocarbon (for example, $C_6F_{13}CH_2CH_3$ (for example, ASAHIKLIN (registered trademark) AC-6000 manufactured by Asahi Glass Co., Ltd.), 1,1,2,2,3,3,4-heptafluorocyclopentane (for example, ZEORORA (registered trademark) H manufactured by Nippon Zeon Co., Ltd.); a hydrofluoroether (HFE) (for example, an alkyl perfluoroalkyl ether such as perfluoropropyl methyl ether ($C_3F_7OCH_3$) (for example, Novec (trademark) 7000 manufactured by Sumitomo 3M Ltd.), perfluorobutyl methyl ether ($C_4F_9OCH_3$) (for example, Novec (trademark) 7100 manufactured by Sumitomo 3M Ltd.), perfluorobutyl ethyl ether ($C_4F_9OC_2H_5$) (for example, Novec (trademark) 7200 manufactured by Sumitomo 3M Ltd.), and perfluorohexyl methyl ether ($C_2F_5CF(OCH_3)C_3F_7$) (for example, Novec (trademark) 7300 manufactured by Sumitomo 3M Ltd.) (the perfluoroalkyl group and the alkyl group may be liner or branched)), or $CF_3CH_2OCF_2CHF_2$ (for example, ASAHIKLIN (registered trademark) AE-3000 manufactured by Asahi Glass Co., Ltd.) and the like. These solvents may be used alone or as a mixture of 2 or more compound. Among them, the hydrofluoroether is preferable, perfluorobutyl methyl ether ($C_4F_9OCH_3$) and/or perfluorobutyl ethyl ether ($C_4F_9OC_2H_5$) are particularly preferable.

When the dry coating method is used, the surface-treating agent of the present invention may be directly subjected to the dry coating method, or may be diluted with a solvent, and then subjected to the dry coating method.

The formation of the film is preferably performed so that the surface-treating agent of the present invention is present together with a catalyst for hydrolysis and dehydration-condensation in the coating. Simply, when the wet coating method is used, after the surface-treating agent of the present invention is diluted with a solvent, and just prior to applying it to the surface of the base material, the catalyst may be added to the diluted solution of the surface-treating agent of the present invention. When the dry coating method is used, the surface-treating agent of the present invention to which a catalyst has been added is used itself in deposition (usually, vacuum deposition), or pellets may be used in the deposition (usually, the vacuum deposition), wherein the pellets is obtained by impregnating a porous metal such as iron or copper with the surface-treating agent of the present invention to which the catalyst has been added.

As the catalyst, any suitable acid or base can be used. As the acid catalyst, for example, acetic acid, formic acid, trifluoroacetic acid, or the like can be used. As the base catalyst, for example, ammonia, an organic amine, or the like can be used.

Next, the film is post-treated as necessary. This post-treatment is, but not limited to, a treatment in which water supplying and dry heating are sequentially performed, in more particular, may be performed as follows.

After the film of the surface-treating agent of the present invention is formed on the surface of the base material as mentioned above, water is supplied to this film (hereinafter, referred to as precursor coating). The method of supplying water may be, for example, a method using dew condensation due to the temperature difference between the precursor coating (and the base material) and ambient atmosphere or spraying of water vapor (steam), but not specifically limited thereto.

It is considered that, when water is supplied to the precursor coating, water acts on a hydrolyzable group bonding to Si present in the perfluoro(poly)ether group containing silane compound in the surface-treating agent of the present invention, thereby enabling rapid hydrolysis of the compound.

The supplying of water may be performed under an atmosphere, for example, at a temperature of zero to 500° C., preferably 100° C. or more and 300° C. or less. By supplying water at such temperature range, hydrolysis can proceed. The pressure at this time is not specifically limited but simply may be ambient pressure.

Then, the precursor coating is heated on the surface of the base material under a dry atmosphere over 60° C. The method of dry heating may be to place the precursor coating together with the base material in an atmosphere at a temperature over 60° C., preferably over 100° C., and for example, of 500° C. or less, preferably of 300° C. or less, and at unsaturated water vapor pressure, but not specifically limited thereto. The pressure at this time is not specifically limited but simply may be ambient pressure.

Under such atmosphere, between the PFPE containing silane compound of the present inventions, the groups (being hydroxyl groups when all $R^1$ are hydroxyl groups in the above mentioned compound of any of the formula (1a) and (1b); hereinafter the same shall apply) bonding to Si after hydrolysis are rapidly dehydration-condensed with each other. Furthermore, between the compound and the base material, the group bonding to Si in the compound after hydrolysis and a reactive group present on the surface of the base material are rapidly reacted, and when the reactive group present on the surface of the base material is a hydroxyl group, dehydration-condensation is caused. As the result, the bond between the PFPE containing silane compounds of the present invention is formed, and the bond between the compound and the base material is formed. It is noted that if present, the fluorine-containing oil and/or the silicone oil is held or acquired by an affinity to the perfluoropolyether group containing silane compound.

The above supplying of water and dry heating may be sequentially performed by using a superheated water vapor.

The superheated water vapor is a gas which is obtained by heating a saturated water vapor to a temperature over the boiling point, wherein the gas, under an ambient pressure, has become to have a unsaturated water vapor pressure by heating to a temperature over 100° C., generally of 500° C. or less, for example, of 300° C. or less, and over the boiling point. When the base material on which the precursor coating is formed is exposed to a superheated water vapor, firstly, due to the temperature difference between the superheated water vapor and the precursor coating of a relatively low temperature, dew condensation is generated on the surface of the precursor coating, thereby supplying water to the precursor coating. Presently, as the temperature difference between the superheated water vapor and the precursor coating decreases, water on the surface of the precursor coating is evaporated under the dry atmosphere of the superheated water vapor, and an amount of water on the surface of the precursor coating gradually decreases. During the amount of water on the surface of the precursor coating is decreasing, that is, during the precursor coating is under the dry atmosphere, the precursor coating on the surface of the base material contacts with the superheated water vapor, as a result, the precursor coating is heated to the temperature of the superheated water vapor (temperature over 100° C. under ambient pressure). Therefore, by using a superheated water vapor, supplying of water and dry heating are enabled to be sequentially carried out simply by exposing the base material on which the precursor coating is formed to a superheated water vapor.

As mentioned above, the post-treatment can be performed. It is noted that though the post-treatment may be performed in order to further increase friction durability, it is not essential in the producing of the article of the present invention. For example, after applying the surface-treating agent to the surface of the base material, it may be enough to only stand the base material.

As described above, the surface-treating layer derived from the film of the surface-treating agent of the present invention is formed on the surface of the base material to produce the article of the present invention. The surface-treating layer thus formed has high surface slip property and high friction durability. Furthermore, this surface-treating layer may have water-repellency, oil-repellency, antifouling property (for example, preventing from adhering a fouling such as fingerprints), surface slip property (or lubricity, for example, wiping property of a fouling such as fingerprints and excellent tactile feeling in a finger) depending on a composition of the surface-treating agent used, in addition to high friction durability, thus may be suitably used as a functional thin film.

Therefore, the present invention further provides an optical material having the hardened material on the outermost layer.

Examples of the optical material include preferably a variety of optical materials in addition to the optical material for displays, or the like exemplified in below: for example, displays such as a cathode ray tube (CRT; for example, TV, personal computer monitor), a liquid crystal display, a plasma display, an organic EL display, an inorganic thin-film EL dot matrix display, a rear projection display, a vacuum fluorescent display (VFD), a field emission display (FED; Field Emission Display), or a protective plate of such displays, or that in which these displays and protective plates have been subjected to antireflection treatment on their surface.

The article having the surface-treating layer obtained according to the present invention is not specifically limited to, but may be an optical member. Examples of the optical member include the followings: lens of glasses, or the like; a front surface protective plate, an antireflection plate, a polarizing plate, or an anti-glare plate on a display such as PDP and LCD; a touch panel sheet of an instrument such as a mobile phone or a personal digital assistance; a disk surface of an optical disk such as a Blu-ray disk, a DVD disk, a CD-R or MO; an optical fiber, and the like.

The article having the surface-treating layer obtained according to the present invention may be also a medical equipment or a medical material.

The thickness of the surface-treating layer is not specifically limited. For the optical member, the thickness of the surface-treating layer is within the range of 1-30 nm, preferably 1-15 nm, in view of optical performance, friction durability and antifouling property.

Hereinbefore, the article produced by using the surface-treating agent of the present invention is described in detail. It is noted that an application, a method for using or a method for producing the article are not limited to the above exemplification.

EXAMPLES

The perfluoro(poly)ether group containing silane compound, the process for producing it and the surface-treating agent comprising it according to the present invention will be described in detail through Examples, although the present invention is not limited to Examples. It is noted that in Examples, the occurrence order of the four repeating units $(CF_2O)$, $(CF_2CF_2O)$, $(CF_2CF_2CF_2O)$ and $(CF_2CF_2CF_2CF_2O)$ constituting perfluoroether of is not limited.

Synthesis Example

Perfluoropolyether group containing silane compounds were synthesized according to the procedures of Synthesis Examples 1-7.

Synthesis Example 1

To a four necked flask of 100 mL provided with a reflux condenser, a thermometer and a stirrer, perfluoroether modified allyloxy compound (20 g) represented by an average composition: $CF_3CF_2CF_2O(CF_2CF_2CF_2O)_{20}CF_2CF_2CH_2OCH_2CH=CH_2$, 1,3-bis(trifluoromethyl)benzene (20 g), triacetoxymethylsilane (0.06 g), and trichlorosilane (1.36 g) were added and stirred under a nitrogen streaming at 5° C. for 30 minutes. Subsequently, after adding a xylene solution (0.094 ml) containing Pt complex of 1,3-divinyl-1,1,3,3-tetramethyldisiloxane at 2%, the solution was warmed to 60° C. and stirred at this temperature for 5 hours. Then, a volatile content was evaporated under a reduced pressure to obtain the following perfluoropolyether group containing silane compound (A) having trichlorosilane at its terminal (19 g).

Perfluoropolyether Group Containing Silane Compound (A):

Synthesis Example 2

To a four necked flask of 100 mL provided with a reflux condenser, a thermometer and a stirrer, perfluoropolyether group containing silane compound (A) (19 g) having trichlorosilane at its terminal synthesized in Synthesis Example 1 and 1,3-bis(trifluoromethyl)benzene (20 g) were added and stirred under a nitrogen streaming at 5° C. for 30 minutes. Subsequently, 26.4 ml of diethyl ether solution containing allyl magnesium bromide (0.7 mol/L) was added, and the solution was warmed to room temperature and stirred at this temperature for 10 hours. Then, after cooling the solution to 5° C. and adding methanol (5 ml), the solution was warmed to a room temperature and insoluble materials were filtered. Then, after a volatile content was evaporated under a reduced pressure, a nonvolatile fraction was diluted with perfluorohexane, and washing operation with methanol in a separatory funnel was conducted three times (more specifically, the operation in which the perfluoro compounds were maintained in the perfluorohexane phase (the fluorous phase), and the non-fluoro compounds were separated and removed into the methanol phase (the organic phase)). Then, a volatile content was evaporated under a reduced pressure to obtain the following perfluoropolyether group containing allyl compound (B) having an allyl group at its terminal (20 g).

Perfluoropolyether Group Containing Allyl Compound (B):

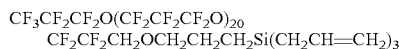

$CF_3CF_2CF_2O(CF_2CF_2CF_2O)_{20}$
$CF_2CF_2CH_2OCH_2CH_2CH_2Si(CH_2CH{=}CH_2)_3$

Synthesis Example 3

To a four necked flask of 100 mL provided with a reflux condenser, a thermometer and a stirrer, perfluoropolyether group containing allyl compound (B) (15 g) having an allyl group at its terminal synthesized in Synthesis Example 2, 1,3-bis(trifluoromethyl)benzene (15 g), triacetoxymethylsilane (0.05 g), and trichlorosilane (3.15 g) were added and stirred under a nitrogen streaming at 5° C. for 30 minutes. Subsequently, after adding a xylene solution (0.141 ml) containing Pt complex of 1,3-divinyl-1,1,3,3-tetramethyldisiloxane at 2%, the solution was warmed to 60° C. and stirred at this temperature for 5 hours. Then, a volatile content was evaporated under a reduced pressure to obtain perfluoropolyether group containing trichlorosilane compound (C) having trichlorosilane at its terminal (16 g).

Perfluoropolyether Group Containing Trichlorosilane Compound (C):

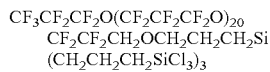

$CF_3CF_2CF_2O(CF_2CF_2CF_2O)_{20}$
$CF_2CF_2CH_2OCH_2CH_2CH_2Si$
$(CH_2CH_2CH_2SiCl_3)_3$

Synthesis Example 4

To a four necked flask of 100 mL provided with a reflux condenser, a thermometer and a stirrer, perfluoropolyether group containing trichlorosilane compound (c) (16 g) having trichlorosilane at its terminal synthesized in Synthesis Example 3 and 1,3-bis(trifluoromethyl)benzene (15 g) were added and stirred under a nitrogen streaming at 50° C. for 30 minutes. Subsequently, after a mixed solution of methanol (0.78 g) and trimethyl orthoformate (36 g) was added, the solution was warmed to 65° C. and stirred at this temperature for 3 hours. Then, a volatile content was evaporated under a reduced pressure to obtain the following perfluoropolyether group containing silane compound (D) having a trimethylsilyl group at its terminal (17 g).

Perfluoropolyether Group Containing Silane Compound (D):

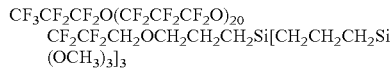

$CF_3CF_2CF_2O(CF_2CF_2CF_2O)_{20}$
$CF_2CF_2CH_2OCH_2CH_2CH_2Si[CH_2CH_2CH_2Si$
$(OCH_3)_3]_3$

Synthesis Example 5

To a four necked flask of 50 mL provided with a reflux condenser, a thermometer and a stirrer, perfluoropolyether group containing silane compound (A) (10 g) having trichlorosilane at its terminal synthesized in Synthesis Example 1 and 1,3-bis(trifluoromethyl)benzene (10 g) were added and stirred under a nitrogen streaming at 5° C. for 30 minutes. Subsequently, 7.06 ml of a diethyl ether solution containing allyl magnesium bromide (0.7 mol/L) was added, and the solution was warmed to a room temperature and stirred at this temperature for 10 hours. Then, after cooling the solution to 5° C. and adding methanol (4 ml), the solution was warmed to a room temperature and insoluble materials were filtered. Subsequently, after a volatile content was evaporated under a reduced pressure, a nonvolatile fraction was diluted with perfluorohexane, and washing operation with methanol in a separatory funnel was conducted three times (more specifically, the operation in which the perfluoro compounds were maintained in the perfluorohexane phase (the fluorous phase), and the non-fluoro compounds were separated and removed into the methanol phase (the organic phase)). Subsequently, a volatile content was evaporated under a reduced pressure to obtain a mixture (E) of the following perfluoropolyether group containing allyl compound having an allyl group at its terminal (9 g).

Mixture of Perfluoropolyether Group Containing Allyl Compound (E):

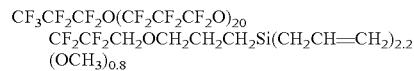

$CF_3CF_2CF_2O(CF_2CF_2CF_2O)_{20}$
$CF_2CF_2CH_2OCH_2CH_2CH_2Si(CH_2CH{=}CH_2)_{2.2}$
$(OCH_3)_{0.8}$

Synthesis Example 6

To a four necked flask of 50 mL provided with a reflux condenser, a thermometer and a stirrer, perfluoropolyether group containing allyl compound (E) (5 g) having an allyl group at its terminal synthesized in Synthesis Example 5, 1,3-bis(trifluoromethyl)benzene (7 triacetoxymethylsilane (0.02 g), and trichlorosilane (1.30 g) were added and stirred under a nitrogen streaming at 5° C. for 30 minutes. Subsequently, after adding a xylene solution (0.045 ml) containing Pt complex of 1,3-divinyl-1,1,3,3-tetramethyldisiloxane at 2%, the solution was warmed to 60° C. and stirred at this temperature for 5 hours. Then, a volatile content was evaporated under a reduced pressure to obtain a mixture of perfluoropolyether group containing trichlorosilane compound (F) having trichlorosilane at its terminal (6 g).

Mixture of Perfluoropolyether Group Containing Trichlorosilane Compound (F):

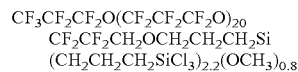

$CF_3CF_2CF_2O(CF_2CF_2CF_2O)_{20}$
$CF_2CF_2CH_2OCH_2CH_2CH_2Si$
$(CH_2CH_2CH_2SiCl_3)_{2.2}(OCH_3)_{0.8}$

Synthesis Example 7

To a four necked flask of 50 mL provided with a reflux condenser, a thermometer and a stirrer, the mixture of perfluoropolyether group containing trichlorosilane compound (F) (6 g) having trichlorosilane at its terminal synthesized in Synthesis Example 6 and 1,3-bis(trifluoromethyl)benzene (6 g) were added and stirred under a nitrogen streaming at 50° C. for 30 minutes. Subsequently, after a mixed solution of methanol (0.21 g) and trimethyl orthoformate (10 g) was added, the solution was warmed to 65° C. and stirred at this temperature for 2 hours. Subsequently, a volatile content was evaporated under a reduced pressure to obtain a mixture of the following perfluoropolyether group containing silane compound (G) having a trimethylsilyl group at its terminal (5 g)

Mixture of Perfluoropolyether Group Containing Silane Compound (G):

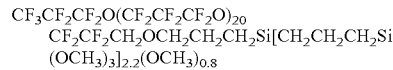

$CF_3CF_2CF_2O(CF_2CF_2CF_2O)_{20}$
$CF_2CF_2CH_2OCH_2CH_2CH_2Si[CH_2CH_2CH_2Si$
$(OCH_3)_3]_{2.2}(OCH_3)_{0.8}$

Synthesis Example 8

To a three necked flask of 50 mL provided with a reflux condenser, a thermometer and a stirrer, perfluoropolyether group containing trichlorosilane compound (c) (2.5 g) having trichlorosilane at its terminal synthesized in Synthesis Example 3 and 1,3-bis(trifluoromethyl)benzene (3.0 g) were added and stirred under a nitrogen streaming at 5° C. for 30 minutes. Subsequently, 9.0 ml of a diethyl ether solution containing allyl magnesium bromide (0.7 mol/L) was added, and the solution was warmed to a room temperature and stirred at this temperature for 10 hours. Then, after cooling the solution to 5° C. and adding methanol (2 ml), the solution was warmed to a room temperature and insoluble materials were filtered. Subsequently, after a volatile content was evaporated under a reduced pressure, a nonvolatile fraction was diluted with perfluorohexane, and washing operation with methanol in a separatory funnel was conducted three times (more specifically, the operation in which the perfluoro compounds were maintained in the perfluorohexane phase (the fluorous phase), and the non-fluoro compounds were separated and removed into the methanol phase (the organic phase)). Then, a volatile content was evaporated under a reduced pressure to obtain the following perfluoropolyether group containing allyl compound (H) having an allyl group at its terminal (2.2 g).

Perfluoropolyether Group Containing Allyl Compound (H):

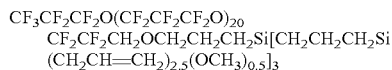

Synthesis Example 9

To a three necked flask of 50 mL provided with a reflux condenser, a thermometer and a stirrer, perfluoropolyether group containing allyl compound (H) (2.2 g) having an allyl group at its terminal synthesized in Synthesis Example 8, 1,3-bis(trifluoromethyl)benzene (5.0 g), triacetoxymethylsilane (7.0 mg) and trichlorosilane (1.5 g) were added and stirred under a nitrogen streaming at 5° C. for 30 minutes. Subsequently, after adding a xylene solution (0.04 ml) containing Pt complex of 1,3-divinyl-1,1,3,3-tetramethyldisiloxane at 2%, the solution was warmed to 60° C. and stirred at this temperature for 5 hours. Then, a volatile content was evaporated under a reduced pressure to obtain the following perfluoropolyether group containing trichlorosilane compound (I) having trichlorosilane at its terminal (2.2 g).

Perfluoropolyether Group Containing Trichlorosilane Compound (I):

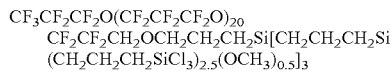

Synthesis Example 10

To a three necked flask of 50 mL provided with a reflux condenser, a thermometer and a stirrer, perfluoropolyether group containing trichlorosilane compound (I) (2.2 g) having trichlorosilane at its terminal synthesized in Synthesis Example 9 and 1,3-bis(trifluoromethyl)benzene (5.0 g) were added and stirred under a nitrogen streaming at 50° C. for 30 minutes. Subsequently, after a mixed solution of methanol (0.5 g) and trimethyl orthoformate (17 g) was added, the solution was warmed to 65° C. and stirred at this temperature for 3 hours. Then, the solution was warmed to a room temperature and insoluble materials were filtered. A volatile content was evaporated under a reduced pressure to obtain the following perfluoropolyether group containing silane compound (J) having a trimethylsilyl group at its terminal (1.9 g).

Perfluoropolyether Group Containing Silane Compound (J):

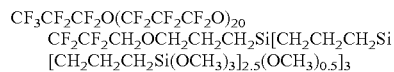

Synthesis Example 11

To a four necked flask of 100 mL provided with a reflux condenser, a thermometer and a stirrer, perfluoroether modified alcohol compound (30 g) represented by an average composition: $CF_3O(CF_2CF_2O)_{15}(CF_2O)_{16}CF_2CH_2OH$ (proviso with, the mixture contains a slight amount of compounds comprising a slight amount of repeating units of $(CF_2CF_2CF_2O)$ and/or $(CF_2CF_2CF_2O)$), 1,3-bis(trifluoromethyl)benzene (20 g) and NaOH (0.8 g) were added and stirred at 65° C. for 4 hours. Then, allyl bromide (2.4 g) was added, and the solution was stirred at 65° C. for 6 hours. Then, the solution was cooled to a room temperature. Perfluorohexane (20 g) was added, and insoluble materials were filtered. Washing operation with 3N hydrochloric acid in a separatory funnel was conducted three times (more specifically, the operation in which the perfluoro compounds were maintained in the perfluorohexane phase (the fluorous phase), and the non-fluoro compounds were separated and removed into the hydrochloric acid phase (the aqueous phase)). Then, a volatile content was evaporated under a reduced pressure to obtain the following perfluoropolyether group containing allyloxy compound (K) having an allyloxy group at its terminal (24 g).

Perfluoropolyether Group Containing Allyloxy Compound (K):

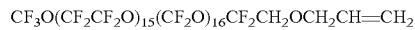

Synthesis Example 12

To a four necked flask of 100 mL provided with a reflux condenser, a thermometer and a stirrer, perfluoropolyether group containing allyloxy compound (K) having an allyloxy group at its terminal (20 g) synthesized in Synthesis Example 11, 1,3-bis(trifluoromethyl)benzene (20 g), triacetoxymethylsilane (0.06 g) and trichlorosilane (1.80 g) were added and stirred under a nitrogen streaming at 5° C. for 30 minutes. Then, after adding a xylene solution (0.10 ml) containing Pt complex of 1,3-divinyl-1,1,3,3-tetramethyldisiloxane at 2%, the solution was warmed to 60° C. and stirred at this temperature for 5 hours. Then, a volatile content was evaporated under a reduced pressure to obtain the following perfluoropolyether group containing silane compound (L) having trichlorosilane at the terminal (20 g).

Perfluoropolyether Group Containing Silane Compound (L):

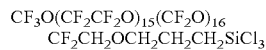

Synthesis Example 13

To a four necked flask of 100 mL provided with a reflux condenser, a thermometer and a stirrer, perfluoropolyether group containing trichlorosilane compound (L) having trichlorosilane at the terminal in Synthesis Example 12 (20 g) and 1,3-bis(trifluoromethyl)benzene (20 g) were added and stirred under a nitrogen streaming at 5° C. for 30 minutes. Then, 35.2 ml of diethyl ether solution containing allyl magnesium bromide (0.7 mol/L) was added, and the solution was warmed to a room temperature and stirred at this temperature for 10 hours. Then, after cooling the solution to 5° C. and adding methanol (5 ml), the solution was warmed to a room temperature and insoluble materials were filtered. Then, after a volatile content was evaporated under a reduced pressure, a nonvolatile fraction was diluted with perfluorohexane, and washing operation with methanol in a separatory funnel was conducted three times (more specifically, the operation in which the perfluoro compounds were maintained in the perfluorohexane phase (the fluorous phase), and the non-fluoro compounds were separated and removed into the methanol phase (the organic phase)). Subsequently, a volatile content was evaporated under a reduced pressure to obtain the following perfluoropolyether group containing allyl compound (M) having an allyl group at its terminal (18 g).

Perfluoropolyether Group Containing Allyl Compound (M):

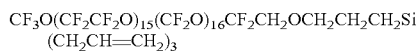
$CF_3O(CF_2CF_2O)_{15}(CF_2O)_{16}CF_2CH_2OCH_2CH_2CH_2Si(CH_2CH=CH_2)_3$ Synthesis Example 14

To a four necked flask of 100 mL provided with a reflux condenser, a thermometer and a stirrer, perfluoropolyether group containing allyl compound (M) (15 g) having an allyl group at its terminal synthesized in Synthesis Example 13, 1,3-bis(trifluoromethyl)benzene (15 g), triacetoxymethylsilane (0.05 g) and trichlorosilane (4.2 g) were added and stirred under a nitrogen streaming at 5° C. for 30 minutes. Subsequently, after adding a xylene solution (0.15 ml) containing Pt complex of 1,3-divinyl-1,1,3,3-tetramethyldisiloxane at 2%, the solution was warmed to 60° C. and stirred at this temperature for 5 hours. Then, a volatile content was evaporated under a reduced pressure to obtain the following perfluoropolyether group containing trichlorosilane compound (N) having trichlorosilane at its terminal (16 g).

Perfluoropolyether Group Containing Trichlorosilane Compound (N):

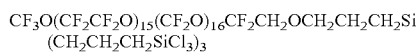
$CF_3O(CF_2CF_2O)_{15}(CF_2O)_{16}CF_2CH_2OCH_2CH_2CH_2Si(CH_2CH_2CH_2SiCl_3)_3$ Synthesis Example 15

To a four necked flask of 100 mL provided with a reflux condenser, a thermometer and a stirrer, perfluoropolyether group containing trichlorosilane compound (N) (16 g) having trichlorosilane at its terminal in synthesized in Synthesis Example 14 and 1,3-bis(trifluoromethyl)benzene (15 g) were added and stirred under a nitrogen streaming at 50° C. for 30 minutes. Subsequently, after a mixed solution of methanol (1.04 g) and trimethyl orthoformate (48 g) was added, the solution was warmed to 65° C., and stirred at this temperature for 3 hours. Then, the solution was cooled to a room temperature and insoluble materials were filtered. A volatile content was evaporated under a reduced pressure to obtain the following perfluoropolyether group containing silane compound (O) having a trimethylsilyl group at its terminal (16 g).

Perfluoropolyether Group Containing Silane Compound (O):

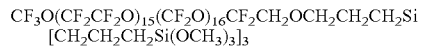
$CF_3O(CF_2CF_2O)_{15}(CF_2O)_{16}CF_2CH_2OCH_2CH_2CH_2Si[CH_2CH_2CH_2Si(OCH_3)_3]_3$ It is noted that in an average composition, although 0.17 repeating units of $(CF_2CF_2CF_2CF_2O)$ and 0.18 repeating unit of $(CF_2CF_2CF_2O)$ were contained, these repeating units were omitted since these amount were slight.

Preparation of a Surface-Treating Agent and Formation of a Surface-Treating Layer (Vacuum Deposition Treatment)

Example 1

Compound (D) was obtained in Synthesis Example 4 was dissolved in hydrofluoroether (Novec HFE7200 manufactured by Sumitomo 3M Ltd.)) such that the concentration was 20 wt % to prepare Surface-treating agent 1.

Surface-treating agent 1 prepared in the above was vacuum deposited on a chemical strengthening glass (Gorilla glass manufactured by Corning Incorporated; thickness: 0.7 mm). Processing condition of the vacuum deposition was a pressure of $3.0 \times 10^{-3}$ Pa. Firstly, silicon dioxide was deposited on the surface of this chemical strengthening glass in a thickness of 7 nm in a manner of an electron-beam deposition to form a silicon dioxide film.

Subsequently, the surface-treating agent of 2 mg (that is, it contained of 0.4 mg of Compound (D)) was vacuum-deposited per one plate of the chemical strengthening glass (55 mm×100 mm). Then, the chemical strengthening glass having the deposited layer was stood at 20° C. under an ambient of humidity of 65% for 24 hours. Thereby, the deposited layer was cured and the surface-treating layer was formed.

Examples 2-4

The surface-treating agent was prepared and the surface-treating layer was formed similarly to Example 1 except that Compound (G) obtained in Synthesis Example 7, Compound (J) obtained in Synthesis Example 10 and Compound (O) obtained in Synthesis Example 15 were used in place of Compound (D), respectively.

Comparative Examples 1-5

The Surface-treating agent was prepared and the surface-treating layer was formed similarly to Example 1 except that the following control compounds 1-5 were used in place of Compound (D), respectively.

Control compound 1

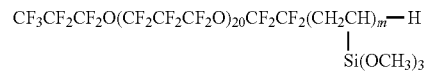
$CF_3CF_2CF_2O(CF_2CF_2CF_2O)_{20}CF_2CF_2(CH_2CH)_m-H$
$\qquad\qquad\qquad\qquad\qquad\qquad\qquad\quad |$
$\qquad\qquad\qquad\qquad\qquad\qquad\qquad\quad Si(OCH_3)_3$ wherein m is an integer of 1-6.

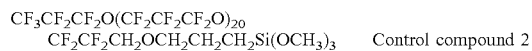
$CF_3CF_2CF_2O(CF_2CF_2CF_2O)_{20}CF_2CF_2CH_2OCH_2CH_2CH_2Si(OCH_3)_3$ Control compound 2

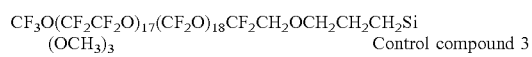
$CF_3O(CF_2CF_2O)_{17}(CF_2O)_{18}CF_2CH_2OCH_2CH_2CH_2Si(OCH_3)_3$ Control compound 3

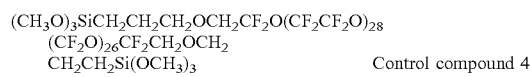
$(CH_3O)_3SiCH_2CH_2CH_2OCH_2CF_2O(CF_2CF_2O)_{28}(CF_2O)_{26}CF_2CH_2OCH_2CH_2CH_2Si(OCH_3)_3$ Control compound 4

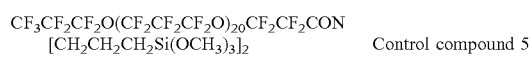
$CF_3CF_2CF_2O(CF_2CF_2CF_2O)_{20}CF_2CF_2CON[CH_2CH_2CH_2Si(OCH_3)_3]_2$ Control compound 5

Experiment 1

Evaluation of Friction Durability

A static water contact angle of the surface-treating layers formed on the surface of the base material in the above Examples and Comparative Examples was measured. The static water contact angle was measured for 1 μL of water by using a contact angle measuring instrument (manufactured by KYOWA INTERFACE SCIENCE Co., Ltd.).

Firstly, as an initial evaluation, the static water contact angle of the surface-treating layer of which the surface had not still contacted with anything after formation thereof was measured (the number of rubbing is zero).

Then, as an evaluation of the friction durability, a steel wool friction durability evaluation was performed. Specifically, the base material on which the surface-treating layer was formed was horizontally arranged, and then, a steel wool (grade No. 0000, dimensions: 5 mm×10 mm×10 mm) was contacted with the exposed surface of the surface-treating layer and a load of 1000 gf was applied thereon. Then, the steel wool was shuttled at a rate of 140 mm/second while applying the load. The static water contact angle (degree) was measured per 1,000 shuttling. The evaluation was stopped when the measured value of the contact angle became to be less than 100 degree.

The results of Examples 1-4 are shown in Table 1, and the results of Comparative Examples 1-5 are shown in Table 2. In the table, a symbol "–" means "not measured".

TABLE 1

| Number of rubbing (times) | Contact Angle (degree) | | | |
|---|---|---|---|---|
| | Example 1 | Example 2 | Example 3 | Example 4 |
| 0 | 115.2 | 115.0 | 115.0 | 115.4 |
| 1000 | 114.9 | 111.1 | 114.0 | 114.2 |
| 2000 | 114.0 | 109.7 | 113.9 | 113.7 |
| 3000 | 113.8 | 108.8 | 113.8 | 113.3 |
| 4000 | 113.8 | 106.9 | 113.4 | 113.3 |
| 5000 | 113.6 | 106.4 | 113.0 | 113.2 |
| 6000 | 113.6 | 106.1 | 112.4 | 113.0 |
| 7000 | 112.9 | 105.5 | 112.3 | 112.8 |
| 8000 | 112.3 | 103.5 | 111.1 | 112.8 |
| 9000 | 111.3 | 101.0 | 110.8 | 111.6 |
| 10000 | 110.9 | 97.2 | 110.3 | 111.2 |
| 11000 | 108.5 | — | 109.6 | 110.5 |
| 12000 | 105.2 | — | 109.0 | 109.4 |
| 13000 | 103.2 | — | 106.3 | 107.4 |
| 14000 | 99.0 | — | 103.7 | 105.8 |
| 15000 | — | — | 93.6 | 104.0 |
| 16000 | — | — | — | 100.5 |
| 17000 | — | — | — | 95.5 |

TABLE 2

| Number of rubbing (times) | Contact Angle (degree) | | | | |
|---|---|---|---|---|---|
| | Comparative Example 1 | Comparative Example 2 | Comparative Example 3 | Comparative Example 4 | Comparative Example 5 |
| 0 | 112.6 | 114.7 | 113.0 | 106.6 | 114.8 |
| 1000 | 111.9 | 102.5 | 110.2 | 89.6 | 107.9 |
| 2000 | 109.5 | 91.5 | 108.7 | — | 105.0 |
| 3000 | 108.4 | — | 102.0 | — | 103.9 |
| 4000 | 105.3 | — | 98.3 | — | 102.2 |
| 5000 | 101.3 | — | — | — | 93.2 |
| 6000 | 97.9 | — | — | — | — |

As understood from Tables 1 and 2, it was confirmed that Examples 1-4 using the perfluoropolyether group containing silane compound of the present invention showed remarkably increased friction durability in comparison with Comparative Examples 1-5 using the conventional perfluoropolyether group containing silane compound.

Example 5

The surface-treating layer was formed similarly to Example 1 except that the amount of the surface-treating agent per one plate of the chemical strengthening glass was 3 mg (that is, it contained of 0.6 mg of Compound (D)).

Example 6

The surface-treating agent was prepared and the surface-treating layer was formed similarly to Example 5 except that Compound (O) was used in place of Compound (D).

Example 7

The surface-treating layer was formed similarly to Example 1 except that the amount of the surface-treating agent per one plate of the chemical strengthening glass was 1.5 mg (that is, it contained of 0.3 mg of Compound (D)).

Example 8

The surface-treating agent was prepared and the surface-treating layer was formed similarly to Example 7 except that Compound (O) was used in place of Compound (D).

Comparative Example 6

The surface-treating agent was prepared and the surface-treating layer was formed similarly to Example 5 except that Control compound 1 was used in place of Compound (D).

Comparative Example 7

The surface-treating agent was prepared and the surface-treating layer was formed similarly to Example 5 except that Control compound 3 was used in place of Compound (D).

Comparative Example 8

The surface-treating agent was prepared and the surface-treating layer was formed similarly to Example 7 except that Control compound 1 was used in place of Compound (D).

Comparative Example 9

The surface-treating agent was prepared and the surface-treating layer was formed similarly to Example 7 except that Control compound 3 was used in place of Compound (D).

Experiment 2

Evaluation of Friction Durability

The static water contact angle of the surface-treating layers formed on the surface of the base material in the above Examples 5-8 and Comparative Examples 6-9 was measured similarly to above Experiment 1. It is noted that with respect to Example 6, since the steel wool was worm at 20,000 shuttling, the evaluation after it could not be continued.

The results of Examples 5-8 are shown in Table 3, and the results of Comparative Examples 6-9 are shown in Table 4. In the table, a symbol "–" means "not measured".

TABLE 3

| Number of rubbing (times) | Contact Angle (degree) | | | |
|---|---|---|---|---|
| | Example 5 | Example 6 | Example 7 | Example 8 |
| 0 | 115.5 | 115.4 | 115.1 | 114.9 |
| 1000 | 114.0 | 114.9 | 114.7 | 114.5 |
| 2000 | 113.8 | 114.5 | 114.5 | 114.1 |
| 3000 | 113.0 | 114.0 | 114.2 | 113.7 |
| 4000 | 112.8 | 113.9 | 114.0 | 113.5 |
| 5000 | 112.6 | 113.8 | 112.4 | 113.5 |
| 6000 | 112.5 | 113.7 | 111.3 | 113.4 |
| 7000 | 112.2 | 113.3 | 108.9 | 112.7 |
| 8000 | 111.9 | 112.9 | 108.6 | 112.2 |
| 9000 | 111.8 | 112.3 | 107.6 | 111.2 |
| 10000 | 109.8 | 111.5 | 107.4 | 110.8 |
| 11000 | 107.8 | 111.2 | 102.9 | 110.2 |
| 12000 | 106.5 | 111.0 | 99.7 | 109.9 |
| 13000 | 103.6 | 109.8 | — | 108.4 |
| 14000 | 97.2 | 109.0 | — | 107.4 |
| 15000 | — | 108.7 | — | 106.9 |
| 16000 | — | 108.2 | — | 105.3 |
| 17000 | — | 108.1 | — | 98.2 |
| 18000 | — | 108.0 | — | — |
| 19000 | — | 107.6 | — | — |
| 20000 | — | 107.1 | — | — |

TABLE 4

| Number of rubbing (times) | Contact Angle (degree) | | | |
|---|---|---|---|---|
| | Comparative Example 6 | Comparative Example 7 | Comparative Example 8 | Comparative Example 9 |
| 0 | 113.0 | 113.5 | 112.5 | 113.1 |
| 1000 | 112.3 | 111.7 | 111.0 | 95.6 |
| 2000 | 111.8 | 106.5 | 105.3 | — |
| 3000 | 109.8 | 105.8 | 101.3 | — |
| 4000 | 107.2 | 98.4 | 92.9 | — |
| 5000 | 106.4 | — | — | — |
| 6000 | 99.8 | — | — | — |

As understood from Tables 1-4, it was confirmed that the surface-treating agent using the perfluoropolyether group containing silane compound of the present invention showed excellent friction durability even when the treating amount was increased to 3 mg (Examples 5 and 6) and even when the treating amount was decreased to 1.5 mg (Examples 7 and 8). In contrast, the surface-treating agent using the conventional perfluoropolyether group containing silane compound, when the treating amount was increased to 3 mg (Comparative Examples 6 and 7), provided the effect similar to when the treating amount was 2 mg (Comparative Examples 1 and 3), but provided the greatly less friction durability than the above surface-treating agent of the present invention. Additionally, when the treating amount was decreased to 1.5 mg (Comparative Examples 8 and 9), the friction durability was very low, in particular, the friction durability for Example 9 was little. From these results, it was confirmed that the surface-treating agent of the present invention could showed excellent friction durability even when the treating amount is small in comparison with the conventional surface-treating agent.

Example 9

The surface-treating layer was formed similarly to Example 1 except that Compound (D) and the following perfluoropolyether compound (P) having an average molecular weight of about 25,000 (FOMBLIN (No.) M60 manufactured by Solvay Co.), at the weight ratio of 2:1, were dissolved in hydrofluoroether (Novec HFE7200 manufactured by Sumitomo 3M Ltd.)) such that the concentration was 20 wt % (total concentration of Compound (D) and Compound (P)) (i.e. the amount of the surface-treating agent per one plate of chemical strengthening glass is 2 mg) to prepare the surface-treating agent.

Perfluoropolyether compound (P)

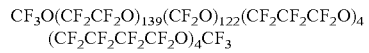

Example 10

The surface-treating agent was prepared and the surface-treating layer was formed similarly to Example 9 except that Compound (O) was used in place of Compound (D).

Example 11

The surface-treating layer was formed similarly to Example 9 except that the amount of the surface-treating agent per one plate of the chemical strengthening glass was 3 mg.

Example 12

The surface-treating layer was formed similarly to Example 11 except that the ratio of Compound (D) to Compound (P) was 1:1 weight ratio in the preparation of the surface-treating agent.

Example 13

The surface-treating layer was formed similarly to Example 11 except that the ratio of Compound (D) to Compound (P) was 1:2 weight ratio in the preparation of the surface-treating agent.

Example 14

The surface-treating layer was formed similarly to Example 10 except that the amount of the surface-treating agent per one plate of the chemical strengthening glass was 3 mg.

Example 15

The surface-treating layer was formed similarly to Example 14 except that the ratio of Compound (O) to Compound (P) was 1:1 weight ratio in the preparation of the surface-treating agent.

Example 16

The surface-treating layer was formed similarly to Example 14 except that the ratio of Compound (O) to Compound (P) was 1:2 weight ratio in the preparation of the surface-treating agent.

Experiment 3

Evaluation of Friction Durability

The static water contact angle of the surface-treating layers formed on the surface of the base material in the above Examples 9-16 was measured similarly to above Experiment 1. It is noted that with respect to Examples 10-12 and 14-16, since the steel wool was worn at 20,000 shuttling, the evaluation could not be continued.

The results are shown in Table 3. In the table, a symbol "–" means "not measured".

Experiment 4

Evaluation of Surface Slip Property

The coefficient of dynamic friction of the surface-treating layers formed on the surface of the base material in the above Examples 1-16 and Comparative Examples 1-9 was measured.

Coefficient of dynamic friction (–) was measured by using a surface texture measurement instrument (FPT-1 manufactured by Labthink Co.) using a paper as a friction probe according to ASTM D1894. Specifically, the base material on which the surface-treating layer was formed was horizontally arranged, and then, a friction paper (2 cm×2 cm) was contacted to an exposed surface of the surface-treating layer and a load of 200 gf was applied thereon. Then, the friction paper was parallely moved at a speed of 500 mm/second while applying the load and the coefficient of dynamic friction was measured.

The results are shown in Table 6.

TABLE 5

| Number of rubbing | Contact Angle (degree) | | | | | | | |
|---|---|---|---|---|---|---|---|---|
| (times) | Example 9 | Example 10 | Example 11 | Example 12 | Example 13 | Example 14 | Example 15 | Example 16 |
| 0 | 115.6 | 115.5 | 115.0 | 115.2 | 115.4 | 115.1 | 115.3 | 115.4 |
| 1000 | 115.4 | 115.3 | 114.8 | 114.4 | 114.8 | 114.7 | 114.2 | 115.0 |
| 2000 | 114.9 | 114.6 | 114.6 | 114.0 | 114.5 | 114.4 | 113.5 | 114.2 |
| 3000 | 114.7 | 114.6 | 114.0 | 113.8 | 114.0 | 114.3 | 113.0 | 114.0 |
| 4000 | 114.6 | 114.1 | 113.9 | 113.6 | 113.0 | 113.8 | 112.8 | 113.8 |
| 5000 | 114.4 | 114.0 | 113.8 | 113.3 | 112.5 | 113.3 | 112.6 | 113.2 |
| 6000 | 114.3 | 114.0 | 113.6 | 113.0 | 111.0 | 113.1 | 112.3 | 113.0 |
| 7000 | 114.1 | 113.8 | 113.5 | 112.9 | 108.6 | 113.0 | 112.1 | 112.2 |
| 8000 | 114.0 | 113.6 | 113.2 | 112.7 | 105.8 | 112.8 | 112.1 | 112.1 |
| 9000 | 113.5 | 113.3 | 113.0 | 112.5 | 100.6 | 112.6 | 112.0 | 112.0 |
| 10000 | 113.2 | 113.2 | 112.7 | 112.0 | 98.0 | 112.2 | 111.0 | 111.8 |
| 11000 | 112.9 | 111.5 | 112.5 | 111.8 | — | 112.0 | 110.0 | 111.7 |
| 12000 | 112.8 | 111.1 | 111.9 | 111.1 | — | 111.8 | 109.7 | 111.4 |
| 13000 | 112.6 | 110.7 | 110.6 | 109.7 | — | 111.7 | 109.0 | 110.2 |
| 14000 | 112.2 | 109.3 | 110.0 | 109.6 | — | 111.5 | 108.5 | 108.0 |
| 15000 | 111.8 | 109.0 | 109.2 | 108.6 | — | 111.3 | 108.3 | 107.6 |
| 16000 | 109.5 | 108.9 | 108.5 | 106.1 | — | 111.1 | 108.0 | 107.3 |
| 17000 | 108.6 | 108.8 | 103.9 | 104.8 | — | 110.8 | 107.8 | 107.0 |
| 18000 | 105.0 | 108.0 | 102.8 | 104.6 | — | 109.9 | 107.1 | 106.5 |
| 19000 | 102.5 | 107.5 | 102.5 | 104.0 | — | 108.9 | 106.5 | 106.0 |
| 20000 | 98.3 | 104.0 | 102.0 | 103.2 | — | 108.8 | 106.3 | 105.8 |

As understood from Table 5, it was confirmed that the friction durability was increased by combining the perfluoropolyether group containing silane compound of the present invention with Compound (P) which is a fluorine-containing oil. Here, for Example 13, the friction durability is 9,000 and less than that for Compound (D) alone. The reason for it is estimated to be that the ratio of Compound (D) to Compound (P) was 1:2, thus the amount of Compound (D) became to be substantially ⅓ and too little. Additionally, the friction durability for Examples 14-16 in which Compound (D) and Compound (P) were combined were not less than 20,000, but if the evaluation is continued, the effect to combine with Compound (P) be estimated to be shown.

TABLE 6

| Example No. | Coefficient of dynamic friction | Comparative Example No. | Coefficient of dynamic friction |
|---|---|---|---|
| Example 1 | 0.068 | Comparative Example 1 | 0.074 |
| Example 2 | 0.069 | Comparative Example 2 | 0.068 |
| Example 3 | 0.068 | Comparative Example 3 | 0.036 |
| Example 4 | 0.036 | Comparative Example 4 | 0.070 |
| Example 5 | 0.068 | Comparative Example 5 | 0.072 |
| Example 6 | 0.036 | Comparative Example 6 | 0.074 |

TABLE 6-continued

| Example No. | Coefficient of dynamic friction | Comparative Example No. | Coefficient of dynamic friction |
|---|---|---|---|
| Example 7 | 0.068 | Comparative Example 7 | 0.036 |
| Example 8 | 0.035 | Comparative Example 8 | 0.074 |
| Example 9 | 0.035 | Comparative Example 9 | 0.035 |
| Example 10 | 0.028 | | |
| Example 11 | 0.034 | | |
| Example 12 | 0.034 | | |
| Example 13 | 0.029 | | |
| Example 14 | 0.027 | | |
| Example 15 | 0.026 | | |
| Example 16 | 0.026 | | |

As understood from Table 6, it was confirmed that the surface-treating agent using the perfluoropolyether group containing silane compound of the present invention provided excellent surface slip property. In particular, when Compound (O) was used (Examples 4, 6 and 8) and when Compound (P) which is a fluorine-containing oil was combined (Examples 9-16), it is confirmed that more excellent slip property was shown.

Preparation of a Surface-Treating Agent and Formation of a Surface-Treating Layer (Spray Treatment)

Example 17

Compound (D) obtained in Synthesis Example 4 was dissolved in hydrofluoroether (Novec HFE7200 manufactured by Sumitomo 3M Ltd.)) such that the concentration was 0.1 wt % to prepare Surface-treating agent 2.

Next, Surface-treating agent 2 above prepared was uniformly spray-coated on a chemical strengthening glass (Gorilla glass manufactured by Corning Incorporated; thickness: 0.7 mm) by using the commercial spray coating equipment equipped with a two-fluid nozzle (head speed: 70 mm/sec). The surface of the chemical strengthening glass was subjected to a plasma treatment using an atmospheric pressure plasma generator (manufactured by Enercon Industries Corporation, Dyne-A-Mite IT) just prior to spray coating. A coating amount of the surface-treating agent was 0.2 ml per one plate of chemical strengthening glass (55 mm×100 mm). Then, the chemical strengthening glass having the spray treated layer was stood under an atmosphere where temperature is 20° C. and humidity is 65% for 48 hours. Thus, the spray treated layer was cured and the surface-treating layer was formed.

Example 18

The surface-treating layer was formed similarly to Example 17 except that Compound (D) and the following perfluoropolyether compound (Q) having an average molecular weight of about 4,000 (FOMBLIN (No.) M03 manufactured by Solvay Co.), at the weight ratio of 2:1, were dissolved in hydrofluoroether (Novec HFE7200 manufactured by Sumitomo 3M Ltd.)) such that the concentration was 0.1 wt % (total concentration of Compound (D) and Compound (Q)) to prepare the surface-treating agent.

Perfluoropolyether Compound (Q)

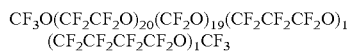
$CF_3O(CF_2CF_2O)_{20}(CF_2O)_{19}(CF_2CF_2CF_2O)_1(CF_2CF_2CF_2CF_2O)_1CF_3$ Example 19

The surface-treating layer was formed similarly to Example 17 except that Compound (D) and the following perfluoropolyether compound (Q) having an average molecular weight of about 4,000 (FOMBLIN (No.) M03 manufactured by Solvay Co.), at the weight ratio of 1:1, were dissolved in hydrofluoroether (Novec HFE7200 manufactured by Sumitomo 3M Ltd.)) such that the concentration was 0.1 wt % (total concentration of Compound (D) and Compound (Q)) to prepare the surface-treating agent.

Example 20

The surface-treating agent was prepared and the surface-treating layer was formed similarly to Example 17 except that Compound (O) obtained the above Synthesis Example 15 was used in place of Compound (D).

Comparative Example 10

The surface-treating agent was prepared and the surface-treating layer was formed similarly to Example 17 except that Control compound 1 was used in place of Compound (D).

Comparative Example 11

The surface-treating layer was formed similarly to Example 17 except that Control compound 1 and the following perfluoropolyether compound (Q) having an average molecular weight of about 4,000 (FOMBLIN (No.) M03 manufactured by Solvay Co.), at the weight ratio of 2:1, were dissolved in hydrofluoroether (Novec HFE7200 manufactured by Sumitomo 3M Ltd.)) such that the concentration was 0.1 wt % (total concentration of Control compound 1 and Compound (Q)) to prepare the surface-treating agent.

Comparative Example 12

The surface-treating layer was formed similarly to Example 17 except that Control compound 1 and the following perfluoropolyether compound (Q) having an average molecular weight of about 4,000 (FOMBLIN (No.) M03 manufactured by Solvay Co.), at the weight ratio of 1:1, were dissolved in hydrofluoroether (Novec HFE7200 manufactured by Sumitomo 3M Ltd.)) such that the concentration was 0.1 wt % (total concentration of Control compound 1 and Compound (Q)) to prepare the surface-treating agent.

Comparative Example 13

The surface-treating agent was prepared and the surface-treating layer was formed similarly to Example 17 except that Control compound 3 was used in place of Compound (D).

Experiment 5

Evaluation of Friction Durability

The static water contact angle of the surface-treating layers formed on the surface of the base material in the above Examples 17-20 and Comparative Examples 10-13 was measured similarly to above Experiment 1.

The results are shown in Table 7. In the table, a symbol "–" means "not measured".

TABLE 7

| Number of rubbing (times) | Contact Angle (degree) | | | | | | | |
|---|---|---|---|---|---|---|---|---|
| | Example 17 | Example 18 | Example 19 | Example 20 | Example 10 | Example 11 | Example 12 | Example 13 |
| 0 | 114.2 | 114.4 | 114.0 | 113.8 | 112.5 | 112.6 | 112.2 | 113.0 |
| 1000 | 113.4 | 113.6 | 113.2 | 112.9 | 108.0 | 106.8 | 103.5 | 107.1 |
| 2000 | 112.6 | 113.1 | 112.8 | 112.4 | 104.7 | 103.5 | 95.5 | 105.2 |
| 3000 | 111.5 | 112.7 | 112.0 | 111.8 | 101.9 | 97.8 | — | 102.7 |
| 4000 | 111.0 | 112.0 | 111.5 | 111.2 | 92.2 | — | — | 96.8 |
| 5000 | 110.8 | 111.5 | 111.0 | 110.4 | — | — | — | — |
| 6000 | 109.6 | 110.8 | 109.9 | 109.5 | — | — | — | — |
| 7000 | 107.9 | 109.3 | 108.6 | 108.2 | — | — | — | — |
| 8000 | 105.8 | 108.9 | 107.2 | 107.1 | — | — | — | — |
| 9000 | 103.5 | 107.4 | 105.8 | 106.5 | — | — | — | — |
| 10000 | 101.8 | 106.5 | 103.6 | 105.1 | — | — | — | — |
| 11000 | 98.6 | 104.4 | 102.8 | 104.6 | — | — | — | — |
| 12000 | — | 103.9 | 94.4 | 103.9 | — | — | — | — |
| 13000 | — | 96.3 | — | 101.6 | — | — | — | — |
| 14000 | — | — | — | 97.1 | — | — | — | — |

Experiment 6

Evaluation of Surface Slip Property

The coefficient of dynamic friction of the surface-treating layers formed on the surface of the base material in the above Examples 17-20 and Comparative Examples 10-13 was measured similarly to Experiment 4.

The results are shown in Table 8.

TABLE 8

| Example No. | Coefficient of dynamic friction | Comparative Example No. | Coefficient of dynamic friction |
|---|---|---|---|
| Example 17 | 0.069 | Comparative Example 10 | 0.072 |
| Example 18 | 0.055 | Comparative Example 11 | 0.065 |
| Example 19 | 0.037 | Comparative Example 12 | 0.050 |
| Example 20 | 0.037 | Comparative Example 13 | 0.038 |

As understood from Table 7, it was confirmed that even when the surface-treating layer was formed by spray treatment, Examples 17-20 using the perfluoropolyether group containing silane compound of the present invention showed remarkably increase friction durability in comparison with Comparative Examples 10-13. Furthermore, from Table 8, even when the surface-treating layer was formed by spray treatment, the surface-treating agent formed by using the perfluoropolyether group containing silane compound of the present invention showed excellent slip property. In particular, when Compound (Q) which is a fluorine-containing oil was combined (Examples 18-19) and when Compound (O) was used (Example 20), it is confirmed that more excellent slip property was shown.

INDUSTRIAL APPLICABILITY

The present invention is suitably applied for forming a surface-treating layer on a surface of various base materials, in particular, an optical member in which transparency is required.

The present invention provides the following embodiments:

1. A perfluoro(poly)ether group containing silane compound of the formula (1a) or the formula (1b):

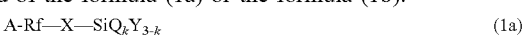
$$A\text{-Rf}—X—SiQ_kY_{3-k} \quad (1a)$$

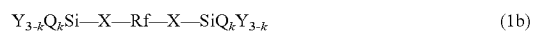
$$Y_{3-k}Q_kSi—X—Rf—X—SiQ_kY_{3-k} \quad (1b)$$

wherein A represents a $C_{1-16}$ alkyl which may be substituted by one or more fluorine atoms;

Rf represents —$(OC_4F_8)_a$—$(OC_3F_6)_b$—$(OC_2F_4)_c$—$(OCF_2)_d$— wherein a, b, c and d are each independently an integer of 0 or more and 200 or less, the sum of a, b, c and d is 1 or more and the occurrence order of the respective repeating units in parentheses with the subscript a, b, c or d is not limited in the formula;

X represents a divalent organic group;

Y represents, each independently at each occurrence, a hydroxyl group, a hydrolyzable group, or a hydrocarbon group;

Q represents, each independently at each occurrence, —Z—$SiR^1_nR^2_{3-n}$;

Z represents, each independently at each occurrence, a divalent organic group: with the proviso that Z is not a group which forms a siloxane bond together with a Si atom present in the end of a molecular backbone of the formula (1a) or the formula (1b), $R^1$ represents, each independently at each occurrence, a hydroxyl group or a hydrolyzable group;

$R^2$ represents, each independently at each occurrence, a $C_{1-22}$ alkyl group or Q';

Q' has the same definition as that of Q;

n is, each independently in each Q and Q', an integer selected from 0-3, and the total sum of n one or more;

in Q, the number of Si atoms which are straightly linked via the Z group is up to five;

k is an integer each independently selected from 1-3.

2. The perfluoro(poly)ether group containing silane compound according to embodiment 1 wherein k is 3.

3. The perfluoro(poly)ether group containing silane compound according to embodiment 1 or 2 wherein the number of Si atoms which are straightly linked via the Z group in Q is one or two.

4. The perfluoro(poly)ether group containing silane compound according to any one of embodiments 1-3 wherein the number of Si atoms which are straightly linked via the Z group in Q is one.

5. The perfluoro(poly)ether group containing silane compound according to any one of embodiments 1-4 wherein A is a $C_{1-16}$ perfluoroalkyl group.

6. The perfluoro(poly)ether group containing silane compound according to any one of embodiments 1-5 wherein Rf is a group of the following formula (a) or (b):

$$—(OC_3F_6)_b— \quad (a)$$

wherein b is an integer of from 1 or more and 200 or less; or $$—(OC_4F_8)_a—(OC_3F_6)_b—(OC_2F_4)_c—(OCF_2)_d— \quad (b)$$

wherein a and b are each independently an integer of 0 or more and 30 or less, c and d are each independently of 1 or more and 200 or less, the sum of a, b, c and d is 10 or more and 200 or less, and the occurrence order of the respective repeating units in parentheses with the subscript a, b, c or d is not limited in the formula.

7. The perfluoro(poly)ether group containing silane compound according to any one of embodiments 1-6 wherein, in Rf:
—$(OC_4F_8)_a$— is —$(OCF_2CF_2CF_2CF_2)_a$—;
—$(OC_3F_6)_b$— is —$(OCF_2CF_2CF_2)_b$—; and
—$(OC_2F_4)_c$— is —$(OCF_2CF_2)_c$—.

8. The perfluoro(poly)ether group containing silane compound according to any one of embodiments 1-7 wherein
X is a group of the formula:

$$—(R^6)_p—(X^1)_q—R^7—$$

wherein:
$R^6$ represents —$(CH_2)_s$— or an o-, m- or p-phenylene group;
$R^7$ represents —$(CH_2)_t$— or an o-, m- or p-phenylene group;
$X^1$ represents —$(X^2)_r$—;
$X^2$ represents, each independently at each occurrence, a group selected from a group consisting of —O—, —S—, an o-, m- or p-phenylene group, —C(O)O—, —CONR$^5$—, —O—CONR$^5$—, —NR$^5$—, —Si(R$^3$)$_2$—, —(Si(R$^3$)$_2$O)$_m$—Si(R$^3$)$_2$— and —(CH$_2$)$_v$—;
$R^3$ represents, each independently at each occurrence, a phenyl group or a $C_{1-6}$ alkyl group;
$R^5$ represents, each independently at each occurrence, a hydrogen atom, a phenyl group or a $C_{1-6}$ alkyl group;
m is, each independently at each occurrence, an integer of 1-100;
v is, each independently at each occurrence, an integer of 1-20;
s is an integer of 1-20;
t is an integer of 1-20;
r is an integer of 1-10;
p is 0 or 1; and
q is 0 or 1.

9. The perfluoro(poly)ether group containing silane compound according to any one of embodiments 1-8 wherein
X is a $C_{1-20}$ alkylene group, —R$^6$—X$^3$—R$^7$—, or —X$^4$—R$^7$—
wherein X$^3$ represents —O—, —S—, —C(O)O—, —CONR$^5$—, —O—CONR$^5$—, —Si(R$^3$)$_2$—, —(Si(R$^3$)$_2$O)$_m$—Si(R$^3$)$_2$—, —O—(CH$_2$)$_u$—CONR$^5$—(CH$_2$)$_v$—N(R$^5$)—, or —CONR$^5$-(o-, m- or p-phenylene)-Si(R$^3$)$_2$—;
X$^4$ represents —S—, —C(O)O—, —CONR$^5$—, —CONR$^5$—(CH$_2$)$_u$—(Si(R$^3$)$_2$O)$_m$—Si(R$^3$)$_2$—, —CONR$^5$—(CH$_2$)$_v$—N(R$^5$)— or —CONR$^5$-(o-, m- or p-phenylene)-Si(R$^3$)$_2$—;
u is an integer of 1-20;
$R^3$, $R^5$, $R^6$, $R^7$, m and v are as defined in embodiment 8.

10. The perfluoro(poly)ether group containing silane compound according to embodiment 8 or 9 wherein $R^6$ is —(CH$_2$)$_s$—, and $R^7$ is —(CH$_2$)$_t$— wherein s and t are as defined in embodiment 8.

11. The perfluoro(poly)ether group containing silane compound according to any one of embodiments 1-10 wherein
X is a $C_{1-20}$ alkylene group, —(CH$_2$)$_s$—O—(CH$_2$)$_t$—, —(CH$_2$)$_s$—(Si(R$^3$)$_2$O)$_m$—Si(R$^3$)$_2$—(CH$_2$)$_t$—, or —(CH$_2$)$_s$—O—(CH$_2$)$_u$—(Si(R$^3$)$_2$O)$_m$—Si(R$^3$)$_2$—(CH$_2$)$_t$—,
wherein $R^3$, s, t and m are as defined in embodiment 8, and u is as defined in embodiment 9.

12. The perfluoro(poly)ether group containing silane compound according to any one of embodiments 1-9 wherein
X is a group selected from a group consisting of:
—CH$_2$O(CH$_2$)$_2$—,
—CH$_2$O(CH$_2$)$_3$—,
—CH$_2$O(CH$_2$)$_6$—,
—CH$_2$O(CH$_2$)$_3$Si(CH$_3$)$_2$OSi(CH$_3$)$_2$(CH$_2$)$_2$—,
—CH$_2$O(CH$_2$)$_3$Si(CH$_3$)$_2$OSi(CH$_3$)$_2$OSi(CH$_3$)$_2$(CH$_2$)$_2$—,
—CH$_2$O(CH$_2$)$_3$Si(CH$_3$)$_2$O(Si(CH$_3$)$_2$O)$_2$Si(CH$_3$)$_2$(CH$_2$)$_2$—,
—CH$_2$O(CH$_2$)$_3$Si(CH$_3$)$_2$O(Si(CH$_3$)$_2$O)$_3$Si(CH$_3$)$_2$(CH$_2$)$_2$—,
—CH$_2$O(CH$_2$)$_3$Si(CH$_3$)$_2$O(Si(CH$_3$)$_2$O)$_{10}$Si(CH$_3$)$_2$(CH$_2$)$_2$—,
—CH$_2$O(CH$_2$)$_3$Si(CH$_3$)$_2$O(Si(CH$_3$)$_2$O)$_{20}$Si(CH$_3$)$_2$(CH$_2$)$_2$—,
—(CH$_2$)$_2$—,
—(CH$_2$)$_3$—,
—(CH$_2$)$_4$—,
—(CH$_2$)$_6$—,
—CONH—(CH$_2$)$_3$—,
—CON(CH$_3$)—(CH$_2$)$_3$—,
—CON(Ph)-(CH$_2$)$_3$— wherein Ph represents a phenyl group,
—CONH—(CH$_2$)$_6$—,
—CON(CH$_3$)—(CH$_2$)$_6$—,
—CON(Ph)-(CH$_2$)$_6$— wherein Ph represents a phenyl group,
—CONH—(CH$_2$)$_2$NH(CH$_2$)$_3$—,
—CONH—(CH$_2$)$_6$NH(CH$_2$)$_3$—,
—CH$_2$O—CONH—(CH$_2$)$_3$—,
—CH$_2$O—CONH—(CH$_2$)$_6$—,
—S—(CH$_2$)$_3$—,
—(CH$_2$)$_2$S(CH$_2$)$_3$—,
—CONH—(CH$_2$)$_3$Si(CH$_3$)$_2$OSi(CH$_3$)$_2$(CH$_2$)$_2$—,
—CONH—(CH$_2$)$_3$Si(CH$_3$)$_2$OSi(CH$_3$)$_2$OSi(CH$_3$)$_2$(CH$_2$)$_2$—,
—CONH—(CH$_2$)$_3$Si(CH$_3$)$_2$O(Si(CH$_3$)$_2$O)$_3$Si(CH$_3$)$_2$(CH$_2$)$_2$—,
—CONH—(CH$_2$)$_3$Si(CH$_3$)$_2$O(Si(CH$_3$)$_2$O)$_{10}$Si(CH$_3$)$_2$(CH$_2$)$_2$—,
—CONH—(CH$_2$)$_3$Si(CH$_3$)$_2$O(Si(CH$_3$)$_2$O)$_{20}$Si(CH$_3$)$_2$(CH$_2$)$_2$—,
—C(O)O—(CH$_2$)$_3$—,
—C(O)O—(CH$_2$)$_6$—,

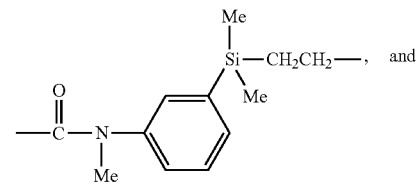 and

-continued

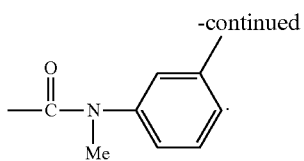

13. The perfluoro(poly)ether group containing silane compound according to any one of embodiments 1-12 wherein Y is, each independently at each occurrence, a group selected from a group consisting of a hydroxyl group, —O($R^5$) wherein $R^5$ represents a $C_{1-12}$ alkyl group, a $C_{1-12}$ alkyl group, a $C_{2-12}$ alkenyl group, a $C_{2-12}$ alkynyl group and a phenyl group.

14. The perfluoro(poly)ether group containing silane compound according to any one of embodiments 1-13 wherein Y is, each independently at each occurrence, a hydroxyl group or an —O($R^5$) wherein $R^5$ represents a $C_{1-12}$ alkyl group.

15. The perfluoro(poly)ether group containing silane compound according to any one of embodiments 1-13 wherein n is 3 in Q.

16. The perfluoro(poly)ether group containing silane compound according to any one of embodiments 1-15 wherein A is a $C_{1-16}$ perfluoroalkyl group;

Rf is a group of the following formula (a) or (b):

$$—(OC_3F_6)_b— \quad (a)$$

wherein b is an integer of 1 or more and 200 or less; or $$—(OC_4F_8)_a—(OC_3F_6)_b—(OC_2F_4)_c—(OCF_2)_d— \quad (b)$$

wherein a and b are each independently an integer of 0 or more and 30 or less, c and d are each independently an integer of 1 or more and 200 or less, the sum of a, b, c and d is 10 or more and 200 or less, and the occurrence order of the respective repeating units in parentheses with the subscript a, b, c or d is not limited in the formula;

X is a $C_{1-20}$ alkylene group, —$(CH_2)_s$—O—$(CH_2)_t$—, —$(CH_2)_s$—$(Si(R^3)_2O)_m$—$Si(R^3)_2$—$(CH_2)_t$— or —$(CH_2)_s$—O—$(CH_2)_u$—$(Si(R^3)_2O)_m$—$Si(R^3)_2$—$(CH_2)_t$— wherein s is an integer of 1-20, t is an integer of 1-20, $R^3$ represents, each independently at each occurrence, a $C_{1-6}$ alkyl group, m is an integer of 1-100, and u is an integer of 1-20;

n is 3, and k is 3.

17. The perfluoro(poly)ether group containing silane compound according to any one of embodiments 1-16 wherein a number average molecular weight of the A-Rf— moiety is 500-30,000.

18. The perfluoro(poly)ether group containing silane compound according to any one of embodiments 1-17 which has a number average molecular weight of 2,000-32,000.

19. A process for producing the perfluoro(poly)ether group containing silane compound of the formula (1a) or the formula (1b) according to embodiment 1, which comprises the following steps:

Step (1): reacting a compound of the formula (1a-1) or the formula (1b-1):

$$\text{A-Rf—X'—CH=CH}_2 \quad (1a-1)$$

$$\text{CH}_2\text{=CH—X'—Rf—X'—CH=CH}_2 \quad (1b-1)$$

wherein A and Rf are as defined in embodiment 1, and X' represents a divalent organic group;

with $HSiM_3$ wherein M is each independently a halogen atom or a $C_{1-6}$ alkoxy group, to obtain a compound of the formula (1a-2) or the formula (1b-2):

$$\text{A-Rf—X'—CH}_2\text{—CH}_2\text{—SiM}_3 \quad (1a-2)$$

$$\text{M}_3\text{Si—CH}_2\text{—CH}_2\text{—X'—Rf—X'—CH}_2\text{—CH}_2\text{—SiM}_3 \quad (1b-2)$$

wherein A, Rf, X' and M are as defined above;

Step (2): reacting a compound of the formula (1a-2) or the formula (1b-2) with a compound of Formula: Hal-J-Z'—CH=$CH_2$ wherein Z' represents a bond or a divalent organic group, J represents Mg, Cu, Pd or Zn, and Hal represents a halogen atom, and optionally a compound of Formula: $Y_hL$ wherein Y is as defined in embodiment 1, L represents a group which is able to bind to Y, and h is an integer of 1-3, to obtain a compound of the formula (1a-3) or the formula (1b-3):

$$\text{A-Rf—X'—CH}_2\text{—CH}_2\text{—Si}(Y_{3-k'})(—Z'—CH=CH_2)_{k'} \quad (1a-3)$$

$$(CH_2=CH—Z'—)_{k'}(Y_{3-k'})Si—CH_2—CH_2—X'—Rf—*$$

$$*X'—CH_2—CH_2—Si(Y_{3-k'})(—Z'—CH=CH_2)_{k'} \quad (1b-3)$$

wherein A, Rf, X', Y and Z' are as defined above, and k' is an integer of 1-3; and Step (3): reacting a compound of the formula (1a-3) or the formula (1b-3) with $HSiM_3$ wherein M is as defined above, and optionally a compound of Formula: $R^1_iL'$ wherein $R^1$ is as defined in embodiment 1, L' represents a group which is able to bind to $R^1$, and i is an integer of 1-3, and/or a compound of Formula: $R^{2'}_jL''$ wherein $R^{2'}$ represents a $C_{1-22}$ alkyl group, L" represents a group which is able to bind to $R^{2'}$, and j is an integer of 1-3.

20. A process for producing the perfluoro(poly)ether group containing silane compound of the formula (1a) or the formula (1b) according to embodiment 1, which comprises the following steps:

Step (1): reacting a compound of the formula (1a-1) or the formula (1b-1):

$$\text{A-Rf—X'—CH=CH}_2 \quad (1a-1)$$

$$\text{CH}_2\text{=CH—X'—Rf—X'—CH=CH}_2 \quad (1b-1)$$

wherein A and Rf are as defined in embodiment 1, and X' represents a divalent organic group;

with $HSiM_3$ wherein M is each independently a halogen atom or a $C_{1-6}$ alkoxy group, to obtain a compound of the formula (1a-2) or the formula (1b-2):

$$\text{A-Rf—X'—CH}_2\text{—CH}_2\text{—SiM}_3 \quad (1a-2)$$

$$\text{M}_3\text{Si—CH}_2\text{—CH}_2\text{—X'—Rf—X'—CH}_2\text{—CH}_2\text{—SiM}_3 \quad (1b-2)$$

wherein A, Rf, X' and M are as defined above;

Step (2'): reacting a compound of the formula (1a-2) or the formula (1b-2) with a compound of Formula: G-Z'—CH=$CH_2$ wherein Z' represents a bond or a divalent organic group, G represents Li, Na or K, and optionally, a compound of
Formula: $Y_hL$ wherein Y is as defined in embodiment 1, L represents a group which is able to bind to Y, and h is an integer of 1-3
to obtain a compound of the formula (1a-3) or the formula (1b-3):

$$A\text{-Rf}-X'-CH_2-CH_2-Si(Y_{3-k'})(-Z'-CH=CH_2)_{k'} \quad (1a\text{-}3)$$

$$(CH_2=CH-Z')_{k'}(Y_{3-k'})Si-CH_2-CH_2-X'-Rf-* $$

$$*X'-CH_2-CH_2-Si(Y_{3-k'})(-Z'-CH=CH_2)_{k'} \quad (1b\text{-}3)$$

wherein A, Rf, X', Y and Z' is as defined above, and k' is an integer of 1-3; and Step (3): reacting a compound of the formula (1a-3) or the formula (1b-3) with $HSiM_3$ wherein M is as defined above, and optionally
a compound of
Formula: $R^1{}_iL'$ wherein $R^1$ is as defined in embodiment 1, L' represents a group which is able to bind to $R^1$, and i is an integer of 1-3, and/or
a compound of
Formula: $R^{2'}{}_jL''$ wherein $R^{2'}$ represents a $C_{1-22}$ alkyl group, L'' represents a group which is able to bind to $R^{2'}$, and j is an integer of 1-3.

21. A compound of the formula (1a-3') or the formula (1b-3'):

$$A\text{-Rf}-X-Si(Y_{3-k'})(-Z'-CH=CH_2)_{k'} \quad (1a\text{-}3')$$

$$(CH_2=CH-Z')_{k'}(Y_{3-k'})Si-X-Rf-*$$

$$*X-Si(Y_{3-k'})(-Z'-CH=CH_2)_{k'} \quad (1b\text{-}3')$$

wherein A represents a $C_{1-16}$ alkyl which may be substituted by one or more fluorine atoms;

Rf represents $-(OC_4F_8)_a-(OC_3F_6)_b-(OC_2F_4)_c-(OCF_2)_d-$ wherein a, b, c and d are each independently an integer of 0 or more and 200 or less, the sum of a, b, c and d is 1 or more, and the occurrence order of the respective repeating units in parentheses with the subscript a, b, c or d is not limited in the formula;

X represents a divalent organic group;

Y represents a hydroxyl group, a hydrolyzable group, or a hydrocarbon group; and Z' is a bond or a divalent organic group.

22. A process for producing the compound of the formula (1a-3') or the formula (1b-3') according to embodiment 21 which comprises a step of:
reacting a compound of the formula (1a-2') or the formula (1b-2'):

$$A\text{-Rf}-X=SiM_3 \quad (1a\text{-}2')$$

$$M_3Si=X-Rf-X-SiM_3 \quad (1b\text{-}2')$$

wherein A, Rf, and X are as defined in embodiment 21, M is a halogen atom or a $C_{2-6}$ alkoxy group,
with a compound of
Formula: Hal-J-Z'—CH=$CH_2$ wherein Z' is as defined in embodiment 6, J represents Mg, Cu, Pd or Zn, and Hal represents a halogen atom, and optionally a compound of
Formula: $Y_hL$ wherein Y is as defined in embodiment 1, L represents a group which is able to bind to Y, and h is an integer of 1-3.

23. A process for producing the compound of the formula (1a-3') or the formula (1b-3') according to embodiment 21 which comprises a step of:

reacting a compound of the formula (1a-2') or the formula (1b-2'):

$$A\text{-Rf}-X-SiM_3 \quad (1a\text{-}2')$$

$$M_3Si-X-Rf-X-SiM_3 \quad (1b\text{-}2')$$

wherein A, Rf, and X are as defined in embodiment 21, and M is a halogen atom or a $C_{1-6}$ alkoxy group,
with a compound of
Formula: G-Z'—CH=$CH_2$ wherein Z' represents a bond or a divalent organic group, and G represents Li, Na or K, and optionally
a compound of
Formula: $Y_hL$ wherein Y is as defined in embodiment 1, L is represents a group which is able to bind to Y, and h is an integer of 1-3.

24. A surface-treating agent comprising at least one the perfluoro(poly)ether group containing silane compound of the formula (1a) and/or the formula (1b) according to any one of embodiments 1-18.

25. The surface-treating agent according to embodiment 24 which further comprises one or more component selected form a fluorine-containing oil, a silicone oil and a catalyst.

26. The surface-treating agent according to embodiment 25 wherein the fluorine-containing oil is one or more compounds of the formula (3):

$$R^{21}-(OC_4F_8)_{a'}-(OC_3F_6)_{b'}-(OC_2F_4)_{c'}-(OCF_2)_{d'}-R^{22} \quad (3)$$

wherein:
$R^{21}$ represents an alkyl group having 1 to 16 carbon atoms which may be substituted by one or more fluorine atoms;
$R^{22}$ represents an alkyl group having 1 to 16 carbon atoms which may be substituted by one or more fluorine atoms, a hydrogen atom or a fluorine atom; and
a', b', c' and d' represent the repeating number of each of four repeating units of perfluoro(poly)ether which constitute a main backbone of the polymer, and are each independently an integer of 0 or more and 300 or less, the sum of a', b', c' and d' is 1 or more, and the occurrence order of the respective repeating units in parentheses with the subscript a', b', c' and d' is not limited in the formula.

27. The surface-treating agent according to embodiment 25 or embodiment 26 wherein the fluorine-containing oil is one or more compounds of the formula (3a) or (3b):

$$R^{21}-(OCF_2CF_2CF_2)_{b''}-R^{22} \quad (3a)$$

$$R^{21}-(OCF_2CF_2CF_2CF_2)_{a''}-(OCF_2CF_2CF_2)_{b''}-(OCF_2CF_2)_{c''}-(OCF_2)_{d''}-R^{22} \quad (3b)$$

wherein:
$R^{21}$ represents an alkyl group having 1 to 16 carbon atoms which may be substituted by one or more fluorine atoms;
$R^{22}$ represents an alkyl group having 1 to 16 carbon atoms which may be substituted by one or more fluorine atoms, a hydrogen atom or a fluorine atom; and
in the formula (3a), b'' is an integer of 1 or more and 100 or less;
in the formula (3b), a'' and b'' are each independently an integer of 0 or more and 30 or less, and c'' and d'' are each independently an integer of 1 or more and 300 or less; and
the occurrence order of the respective repeating units in parentheses with the subscript a'', b'', c'' or d'' is not limited in the formula.

28. The surface-treating agent according to embodiment 27 which comprises one or more compounds of the formula (3b).

29. The surface-treating agent according to embodiment 27 or 28 which comprises the compound of the formula (3a) and the compound of the formula (3b) at a mass ratio of 1:1-1:30.

30. The surface-treating agent according to any one of embodiments 27-29 which comprises the compound of the formula (3a) and the compound of the formula (3b) at a mass ratio of 1:1-1:10.

31. The surface-treating agent according to any one of embodiments 28-30 wherein a mass ratio of at least one the perfluoro(poly)ether group containing silane compound of the formula (1a) or the formula (1b) according to embodiments 1-4 and the compound of the formula (3b) is 4:1-1:4.

32. The surface-treating agent according to any one of embodiments 27-31 wherein the compound of the formula (3a) has a number average molecular weight of 2,000-8,000.

33. The surface-treating agent according to any one of embodiments 27-31 wherein the compound of the formula (3b) has a number average molecular weight of 2,000-30,000.

34. The surface-treating agent according to any one of embodiments 27-31 wherein the compound of the formula (3b) has a number average molecular weight of 8,000-30,000.

35. The surface-treating agent according to any one of embodiments 24-34 which further comprises a solvent.

36. The surface-treating agent according to any one of embodiments 24-35 which is used as an antifouling-coating agent.

37. The surface-treating agent according to any one of embodiments 24-36 for vacuum deposition.

38. A pellet comprising the surface-treating agent according to any one of embodiments 24-37.

39. An article comprising a base material and a layer which is formed on a surface of the base material from the compound according to any one of embodiments 1-18 or the surface-treating agent according to any one of embodiments 24-37.

40. The article according to embodiment 39 which is an optical member.

41. The article according to embodiment 39 which is a display.

The invention claimed is:

1. A perfluoro(poly)ether group containing silane compound of the formula (1a):

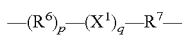  (1a)

wherein A represents a $C_{1-16}$ alkyl which may be substituted by one or more fluorine atoms;

Rf represents 

wherein a, b, c and d are each independently an integer of 0 or more and 200 or less, the sum of a, b, c and d is 1 or more and the occurrence order of the respective repeating units in parentheses with the subscript a, b, c or d is not limited in the formula;

X represents a group of the formula:

—(R$^6$)$_p$—(X$^1$)$_q$—R$^7$— wherein:
R$^6$ represents —(CH$_2$)$_s$— or an o-, m- or p-phenylene group;
R$^7$ represents —(CH$_2$)$_t$— or an o-, m- or p-phenylene group;
X$^1$ represents —(X$^2$)$_r$—;
X$^2$ represents, each independently at each occurrence, a group selected from a group consisting of —O—, —S—, an o-, m- or p-phenylene group, —C(O)O—, —CONR$^5$—, —O—CONR$^5$—, and —(CH$_2$)$_v$—;
R$^5$ represents, each independently at each occurrence, a hydrogen atom, a phenyl group or a $C_{1-6}$ alkyl group;
v is, each independently at each occurrence, an integer of 1-20;
s is an integer of 1-20;
t is an integer of 1-20;
r is an integer of 1-10;
p is 0 or 1; and
q is 0 or 1;
Y represents, each independently at each occurrence, a hydroxyl group, a hydrolyzable group, or a hydrocarbon group provided that Y does not include a silicon atom;
Q represents, each independently at each occurrence, —Z—SiR$^1_n$R$^2_{3-n}$;
Z represents, each independently at each occurrence, a divalent organic group that does not include a silicon atom,
R$^1$ represents, each independently at each occurrence, a hydroxyl group or a hydrolyzable group that does not include a silicon atom;
R$^2$ represents, each independently at each occurrence, a $C_{1-22}$ alkyl group that does not include a silicon atom;
n is, each independently in each Q, an integer selected from 0-3, and the total sum of n in all Q groups is one or more;
k is an integer selected from 2-3.

2. The perfluoro(poly)ether group containing silane compound according to claim 1 to wherein k is 3.

3. The perfluoro(poly)ether group containing silane compound according to claim 1 wherein A is a $C_{1-16}$ perfluoroalkyl group.

4. The perfluoro(poly)ether group containing silane compound according to claim 1 wherein Rf is a group of the following formula (a) or (b):

—(OC$_3$F$_6$)$_b$—  (a)

wherein b is an integer of from 1 or more and 200 or less; or

  (b)

wherein a and b are each independently an integer of 0 or more and 30 or less, c and d are each independently is an integer of 1 or more and 200 or less, the sum of a, b, c and d is 10 or more and 200 or less, and the occurrence order of the respective repeating units in parentheses with the subscript a, b, c or d is not limited in the formula.

5. The perfluoro(poly)ether group containing silane compound according to claim 1 wherein, in Rf:
—(OC$_4$F$_8$)$_a$— is —(OCF$_2$CF$_2$CF$_2$CF$_2$)$_a$—;
—(OC$_3$F$_6$)$_b$— is —(OCF$_2$CF$_2$CF$_2$)$_b$—; and
—(OC$_2$F$_4$)$_c$— is —(OCF$_2$CF$_2$)$_c$—.

6. The perfluoro(poly)ether group containing silane compound according to claim 1 wherein
X is a $C_{1-20}$ alkylene group, —R$^6$—X$^3$—R$^7$—, or —X$^4$—R$^7$—
wherein X$^3$ represents —O—, —S—, —C(O)O—, —CONR$^5$—, —O—CONR$^5$—, or —CONR$^5$—(CH$_2$)$_v$—N(R$^5$)—;
X$^4$ represents —S—, —C(O)O—, —CONR$^5$—, or —CONR$^5$—(CH$_2$)$_v$—N(R$^5$)—.

7. The perfluoro(poly)ether group containing silane compound according to claim 1 wherein R$^6$ is —(CH$_2$)$_s$—, and R$^7$ is —(CH$_2$)$_t$—.

8. The perfluoro(poly)ether group containing silane compound according to claim 1 wherein
X is a $C_{1-20}$ alkylene group or —$(CH_2)_s$—O—$(CH_2)_t$—.

9. The perfluoro(poly)ether group containing silane compound according to claim 1 wherein
X is a group selected from a group consisting of:
—$CH_2O(CH_2)_2$—,
—$CH_2O(CH_2)_3$—,
—$CH_2O(CH_2)_6$—,
—$(CH_2)_2$—,
—$(CH_2)_3$—,
—$(CH_2)_4$—,
—$(CH_2)_6$—,
—CONH—$(CH_2)_3$—,
—CON(CH_3)—$(CH_2)_3$—,
—CON(Ph)-$(CH_2)_3$— wherein Ph represents a phenyl group,
—CONH—$(CH_2)_6$—,
—CON(CH_3)—$(CH_2)_6$—,
—CON(Ph)-$(CH_2)_6$— wherein Ph represents a phenyl group,
—CONH—$(CH_2)_2NH(CH_2)_3$—,
—CONH—$(CH_2)_6NH(CH_2)_3$—,
—$CH_2O$—CONH—$(CH_2)_3$—,
—$CH_2O$—CONH—$(CH_2)_6$—,
—S—$(CH_2)_3$—,
—$(CH_2)_2S(CH_2)_3$—,
—C(O)O—$(CH_2)_3$—,
—C(O)O—$(CH_2)_6$—,
and

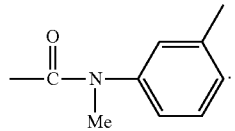

10. The perfluoro(poly)ether group containing silane compound according to claim 1 wherein Y is, each independently at each occurrence, a group selected from a group consisting of a hydroxyl group, —OR(R') wherein R' represents a $C_{1-12}$ alkyl group, a $C_{1-12}$ alkyl group, a $C_{2-12}$ alkenyl group, a $C_{2-12}$ alkynyl group and a phenyl group.

11. The perfluoro(poly)ether group containing silane compound according to claim 1 wherein Y is, each independently at each occurrence, a hydroxyl group or an —O(R') wherein represents a $C_{1-12}$ alkyl group.

12. The perfluoro(poly)ether group containing silane compound according to claim 1 wherein n is 3 in Q.

13. The perfluoro(poly)ether group containing silane compound according to claim 1 wherein
A is a $C_{1-16}$ perfluoroalkyl group;
Rf is a group of the following formula (a) or (b):

$$-(OC_3F_6)_b-\qquad(a)$$

wherein b is an integer of 1 or more and 200 or less; or $$-(OC_4F_8)_a-(OC_3F_6)_b-(OC_2F_4)_c-(OCF_2)_d-\qquad(b)$$

wherein a and b are each independently an integer of 0 or more and 30 or less, c and d are each independently an integer of 1 or more and 200 or less, the sum of a, b, c and d is 10 or more and 200 or less, and the occurrence order of the respective repeating units in parentheses with the subscript a, b, c or d is not limited in the formula;
and
n is 3.

14. The perfluoro(poly)ether group containing silane compound according to claim 1 wherein a number average molecular weight of the A-Rf— moiety is 500-30,000.

15. The perfluoro(poly)ether group containing silane compound according to claim 1 which has a number average molecular weight of 2,000-32,000.

16. The perfluoro(poly)ether group containing silane compound according to claim 6 wherein $R^6$ is —$(CH_2)_s$—, and $R^7$ is —$(CH_2)_t$—.

17. A process for producing the perfluoro(poly)ether group containing silane compound of the formula (1a) according to claim 1, which comprises the following steps:
Step (1): reacting a compound of the formula (1a-1):

$$\text{A-Rf—X'—CH}=CH_2 \qquad (1a-1)$$

wherein A and Rf are as defined in claim 1, and X' represents a divalent organic group;
with $HSiM_3$ wherein M is each independently a halogen atom or a $C_{1-6}$ alkoxy group, to obtain a compound of the formula (1a-2):

$$\text{A-Rf—X'CH}_2\text{—CH}_2\text{—SiM}_3 \qquad (1a-2)$$

wherein A, Rf, X' and M are as defined above;
Step (2'): reacting a compound of the formula (1a-2) with a compound of
Formula: G-Z'—CH=$CH_2$ wherein Z' represents a bond or a divalent organic group, G represents Li, Na or K, and optionally,
a compound of
Formula: $Y_hL$ wherein Y is as defined in claim 1, L represents a group which is able to bind to Y, and h is an integer of 1-3
to obtain a compound of the formula (1a-3):

$$\text{A-Rf—X'—CH}_2\text{—CH}_2\text{—Si}(Y_{3-k'})(\text{—Z'—CH}=CH_2)_{k'} \qquad (1a-3)$$

wherein A, Rf, X', Y and Z' is as defined above, and k' is an integer of 2-3; and
Step (3): reacting a compound of the formula (1a-3) with $HSiM_3$ wherein M is as defined above, and optionally
a compound of
Formula: $R^1_iL'$ wherein $R^1$ is as defined in claim 1, L' represents a group which is able to bind to $R^1$, and i is an integer of 1-3, and/or
a compound of
Formula: $R^2_jL''$ wherein $R^{2'}$ represents a $C_{1-22}$ alkyl group, L'' represents a group which is able to bind to $R^{2'}$, and j is an integer of 1-3.

18. A surface-treating agent comprising at least one the perfluoro(poly)ether group containing silane compound of the formula (1a) according to claim 1.

19. The surface-treating agent according to claim 18 which further comprises one or more component selected form a fluorine-containing oil, a silicone oil and a catalyst.

20. The surface-treating agent according to claim 19, comprising a fluorine-containing oil selected from one or more compounds of the formula (3):

$$R^{21}\text{—}(OC_4F_8)_{a'}\text{—}(OC_3F_6)_{b'}\text{—}(OC_2F_4)_{c'}\text{—}(OCF_2)_{d'}\text{—}R^{22} \qquad (3)$$

wherein:
$R^{21}$ represents an alkyl group having 1 to 16 carbon atoms which may be substituted by one or more fluorine atoms;
$R^{22}$ represents an alkyl group having 1 to 16 carbon atoms which may be substituted by one or more fluorine atoms, a hydrogen atom or a fluorine atom; and a', b', c' and d' are each independently an integer of 0 or more and 300 or less, the sum of a', b', c' and d' is 1 or more, and the occurrence order of the respective repeating units in parentheses with the subscript a', b', c' and d' is not limited in the formula.

21. The surface-treating agent according to claim 19, comprising a fluorine-containing oil selected from one or more compounds of the formula (3a) or (3b):

(3a)

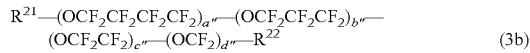

(3b)

wherein:

$R^{21}$ represents an alkyl group having 1 to 16 carbon atoms which may be substituted by one or more fluorine atoms;

$R^{22}$ represents an alkyl group having 1 to 16 carbon atoms which may be substituted by one or more fluorine atoms, a hydrogen atom or a fluorine atom; and in the formula (3a), b" is an integer of 1 or more and 100 or less;

in the formula (3b), a" and b" are each independently an integer of 0 or more and 30 or less, and c" and d" are each independently an integer of 1 or more and 300 or less; and the occurrence order of the respective repeating units in parentheses with the subscript a", b", c" or d" is not limited in the formula.

22. The surface-treating agent according to claim 21 which comprises one or more compounds of the formula (3b).

23. The surface-treating agent according to claim 21 which comprises the compound of the formula (3a) and the compound of the formula (3b) at a mass ratio of 1:1-1:30.

24. The surface-treating agent according to claim 21 which comprises the compound of the formula (3a) and the compound of the formula (3b) at a mass ratio of 1:1-1:10.

25. The surface-treating agent according to claim 22 wherein a mass ratio of the perfluoro(poly)ether group containing silane compound of the formula (1a) and the compound of the formula (3b) is 4:1-1:4.

26. The surface-treating agent according to claim 21 wherein the compound of the formula (3a) has a number average molecular weight of 2,000-8,000.

27. The surface-treating agent according to claim 21 wherein the compound of the formula (3b) has a number average molecular weight of 2,000-30,000.

28. The surface-treating agent according to claim 21 wherein the compound of the formula (3b) has a number average molecular weight of 8,000-30,000.

29. The surface-treating agent according to claim 18 which further comprises a solvent.

30. The surface-treating agent according to claim 18 which is used as an antifouling-coating agent.

31. The surface-treating agent according to claim 18 for vacuum deposition.

32. A pellet comprising the surface-treating agent according to claim 18.

* * * * *